United States Patent [19]
Hu

[11] Patent Number: 6,025,141
[45] Date of Patent: Feb. 15, 2000

[54] IMMUNOFLUORESCENCE ASSAY FOR THE DETECTION OF ANTIBODIES USING RECOMBINANT ANTIGENS IN INSOLUBLE FORM

[75] Inventor: Yu-Wen Hu, Gloucester, Canada

[73] Assignee: The Canadian Red Cross Society, Ottawa, Canada

[21] Appl. No.: 08/392,794

[22] PCT Filed: Dec. 9, 1994

[86] PCT No.: PCT/CA94/00672

§ 371 Date: Sep. 12, 1995

§ 102(e) Date: Sep. 12, 1995

[87] PCT Pub. No.: WO95/16040

PCT Pub. Date: Jun. 15, 1995

Related U.S. Application Data

[63] Continuation-in-part of application No. 08/164,789, Dec. 10, 1993, abandoned.

[51] Int. Cl.[7] .................. G01N 33/53; G01N 33/537; G01N 33/567; C12P 21/06
[52] U.S. Cl. ............... 435/7.1; 435/7.92; 435/5; 435/69.1; 435/69.3; 435/968; 435/971; 435/975; 435/974; 424/184.1; 424/204.1; 424/186.1; 424/187.1; 424/188.1; 424/189.1; 424/806; 530/403; 530/350; 436/513; 436/800
[58] Field of Search .................... 424/880, 801, 424/188.1, 208.1, 184.1, 264.1, 186.1, 187.1, 189.1, 806; 530/403; 536/23.72; 436/513, 800; 435/7.1, 7.2, 7.21, 339.1, 338.35, 7.92, 5, 69.1, 69.3, 968, 971, 975, 974

[56] References Cited

U.S. PATENT DOCUMENTS

| | | |
|---|---|---|
| 4,118,479 | 10/1978 | Prince et al. . |
| 4,129,644 | 12/1978 | McAleer et al. . |
| 4,241,175 | 12/1980 | Miller et al. . |
| 4,722,840 | 2/1988 | Valenzuela et al. . |
| 4,734,362 | 3/1988 | Hung et al. . |
| 4,752,565 | 6/1988 | Folks et al. . |
| 4,870,023 | 9/1989 | Fraser et al. . |
| 4,925,784 | 5/1990 | Crowl et al. . |
| 5,041,385 | 8/1991 | Kingsman et al. . |
| 5,156,949 | 10/1992 | Luciw et al. . |
| 5,169,784 | 12/1992 | Summers et al. . |
| 5,175,098 | 12/1992 | Watanabe et al. . |
| 5,175,099 | 12/1992 | Willis . |
| 5,204,259 | 4/1993 | Helting et al. . |

FOREIGN PATENT DOCUMENTS

| | | |
|---|---|---|
| 0272858 | 6/1988 | European Pat. Off. ........ C12N 15/00 |
| 0307149 | 3/1989 | European Pat. Off. . |

OTHER PUBLICATIONS

Shoeman et al. "Comparison of Recombinant Human Immunodeficeiency Virus gag Precursor and gag/env Fusion Proteins and a Synthetic env Peptide as Diagnostic Reagents". Analytical Biochemistry, vol. 161, pp. 370–379, 1987.

Wagner et al. "Studies on processing, particle formation, and immunogenicity of the HIV–1 gag gene product; a possible component of a HIV vaccine", Arch Virology, vol. 127, pp. 117–137, 1992.

Gaskin et al. "Use of chemical cleavage active HIV–1 proteinase from a fusion protein produced in the form of insoluble inclusion bodies", Biochemical Society Transaction, vol. 20, No. 2, pp. 162S, May 1992.

J.M. Hofbauer et al Journal of Clinical Microbiology, Jan., 1988, 26:116–120, "Comparison of Western Blot (Immunoblot) Based on Recombinant–Derived p41 With Conventional Test for Serodiagnosis of Human Immunodeficiency Virus Infections".

L. Luo et al., Proc. Natl. Acad. Sci. USA, Nov., 1992, 89:10527–10531, "Chimeric gag–V3 Virus–Like Particles of Human Immunodefiency Viorus Induce Virus–Neutralizing Antibodies".

J.M. Sligh et al., A.J.C.P.,Feb., 1989, 91:210–214, "Flow Cytometric Indirect Immunoflorescence Assay with High Sensitivity Specificity for Detection of Anitbodies to Human Immunodeficiency Virus (HIV)".

*Primary Examiner*—Marian C. Knode
*Assistant Examiner*—Datquan Lee
*Attorney, Agent, or Firm*—Browdy and Neimark

[57] ABSTRACT

The present invention relates to the use of insoluble forms of recombinant proteins in a flow cytometric immunofluorescence assay for the detection of given antibodies.

12 Claims, 25 Drawing Sheets

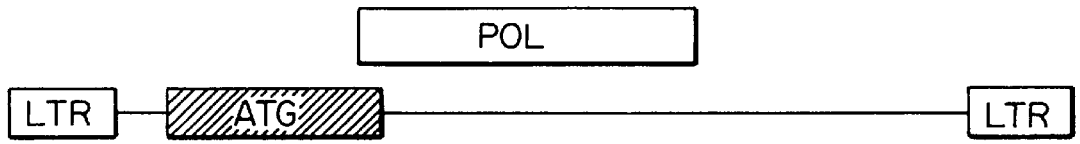
FIG. IA
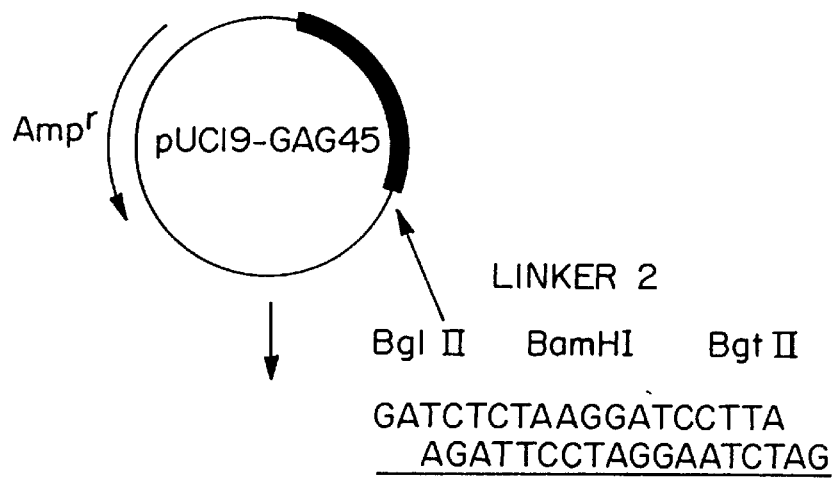
FIG. IB

Nucleotide Sequence of Truncated HIV-1 gag Polyprotein p45

|            |            | GAG        | ATGGGTGCG<br>CDS START |
|------------|------------|------------|------------|
| AGAGCGTCAG | TATTAAGCGG | GGGAGAATTA | GATCGATGGG |
| AAAAAATTCG | GTTAAGGCCA | GGGGGAAAGA | AAAAATATAA |
| ATTAAAACAT | ATAGTATGGG | CAAGCAGGGA | GCTAGAACGA |
| TTCGCAGTTA | ATCCTGGCCT | GTTAGAAACA | TCAGAAGGCT |
| GTAGACAAAT | ACTGGGACAG | CTACAACCAT | CCCTTCAGAC |
| AGGATCAGAA | GAACTTAGAT | CATTATATAA | TACAGTAGCA |
| ACCCTCTATT | GTGTGCATCA | AAGGATAGAG | ATAAAAGACA |
| CCAAGGAAGC | TTTAGACAAG | ATAGAGGAAG | AGCAAAACAA |
| AAGTAAGAAA | AAAGCACAGC | AAGCAGCAGC | TGACACAGGA |
|            | ←P17 P24→  |            |            |
| CACAGCAGTC | AGGTCAGCCA | AAATTACCCT | ATAGTGCAGA |
| ACATCCAGGG | GCAAATGGTA | CATCAGGCCA | TATCACCTAG |
| AACTTTAAAT | GCATGGGTAA | AAGTAGTAGA | AGAGAAGGCT |
| TTCAGCCCAG | AAGTAATACC | CATGTTTTCA | GCATTATCAG |
| AAGGAGCCAC | CCCACAAGAT | TTAAACACCA | TGCTAAACAC |
| AGTGGGGGGA | CATCAAGCAG | CCATGCAAAT | GTTAAAAGAG |
| ACCATCAATG | AGGAAGCTGC | AGAATGGGAT | AGAGTACATC |
| CAGTGCATGC | AGGGCCTATT | GCACCAGGCC | AGATGAGAGA |
| ACCAAGGGGA | AGTGACATAG | CAGGAACTAC | TAGTACCCTT |
| AAGGAACAAA | TAGGATGGAT | GACAAATAAT | CCACCTATCC |
| CAGTAGGAGA | AATTTATAAA | AGATGGATAA | TCCTGGGATT |
| AAATAAAATA | GTAAGAATGT | ATAGCCCTAC | CAGCATTCTG |
| GACATAAGAC | AAGGACCAAA | AGAACCTTTT | AGAGACTATG |
| TAGACCGGTT | CTATAAAACT | CTAAGAGCCG | AGCAAGCTTC |
| ACAGGAGGTA | AAAAATTGGA | TGACAGAAAC | CTTGTTGGTC |
| CAAAATGCGA | ACCCAGATTG | TAAGACTATT | TTAAAAGCAT |

FIG. 2A

| | | | |
|---|---|---|---|
| TGGGACCAGC | GGCTACACTA | GAAGAAATGA | TGACAGCATG |
| | | P24 | P15 |
| TCAGGGAGTA | GGAGGACCCG | GCCATAAGGC | AAGAGTTTTG |
| GCTGAAGCAA | TGAGCCAAGT | AACAAATACA | GCTACCATAA |
| TGATGCAGAG | AGGCAATTTT | AGGAACCAAA | GAAAGATGGT |
| TAAGTGTTTC | AATTGTGGCA | AAGAAGGGCA | CACAGCCAGA |
| AATTGCAGGG | CCCCTAGGAA | AAAGGGCTGT | TGGAAATGTG |
| GAAAGGAAGG | ACACCAAATG | AAAGATTGTA | CTGAGAGACA |
| GGCTAATTTT | TTAGGGAAGA | TCTAA | |

FIG. 2B

Amino Acid Sequence of HIV-1 gag Protein p45

MetGlyAlaArgAlaSerValLeuSerGlyGlyGluLeuAspArgTrpGlu
LysIleArgLeuArgProGlyGlyLysLysLysTyrLysLeuLysHisIle
ValTrpAlaSerArgGluLeuGluArgPheAlaValAsnProGlyLeuLeu
GluThrSerGluGlyCysArgGlnIleLeuGlyGlnLeuGlnProSerLeu
GlnThrGlySerGluGluLeuArgSerLeuTyrAsnThrValAlaThrLeu
TyrCysValHisGlnArgIleGluIleLysAspThrLysGluAlaLeuAsp
LysIleGluGluGluGlnAsnLysSerLysLysLysAlaGlnGlnAlaAla
AlaAspThrGlyHisSerAsnGlnValSerGlnAsnTyrProIleValGln
AsnIleGlnGlyGlnMetValHisGlnAlaIleSerProArgThrLeuAsn
AlaTrpValLysValValGluGluLysAlaPheSerProGluValIlePro
MetPheSerAlaLeuSerGluGlyAlaThrProGlnAspLeuAsnThrMet
LeuAsnThrValGlyGlyHisGlnAlaAlaMetGlnMetLeuLysGluThr
IleAsnGluGluAlaAlaGluTrpAspArgValHisProValHisAlaGly
ProIleAlaProGlyGlnMetArgGluProArgGlySerAspIleAlaGly
ThrThrSerThrLeuGlnGluGlnIleGlyTrpMetThrAsnAsnProPro
IleProValGlyGluIleTyrLysArgTrpIleIleLeuGlyLeuAsnLys
IleValArgMetTyrSerProThrSerIleLeuAspIleArgGlnGlyPro
LysGluProPheArgAspTyrValAspArgPheTyrLysThrLeuArgAla
GluGlnAlaSerGlnGluValLysAsnTrpMetThrGluThrLeuLeuVal
GlnAsnAlaAsnProAspCysLysThrIleLeuLysAlaLeuGlyProAla
AlaThrLeuGluGluMetMetThrAlaCysGlnGlyValGlyGlyProGly
HisLysAlaArgValLeuAlaGluAlaMetSerGlnValThrAsnSerAla
ThrIleMetMetGlnArgGlyAsnPheArgAsnGlnArgLysIleValLys
CysPheAsnCysGlyLysGluGlyHisThrAlaArgAsnCysArgAlaPro
ArgLysLysGlyCysTrpLysCysGlyLysGluGlyHisGlnMetLysAsp
CysThrGluArgGlnAlaAsnPheLeuGlyLysIle

FIG. 3

P1 5' CAG ATC TCC GGA GTA GCA CCC ACC
P2 5' GAG ATC TGT TAA GCA TTC CAA GGC AC
P3 5' CTC GAA GAT CTC CAG GGC TAT TGA GGC GCA
P4 5' CTC GAA GAT CTA TTA CCA CAA ACT TGC CCA

Nucleotide Sequence of Chimeric Protein A

```
gag-p45    GGAGTAGCACCACCAAGGCAAAGAGAGCAAGAGAGAGTGGTGCAGAGAGAAAAAGAGCAGTGGGAATA
  →    +   GlyValAlaProThrLysAlaLysArgAlaArgValValGlnArgGluLysArgAlaValGlyIle GGAGCTTTGTTCCTTGGTTCTTGGGTTCCTTGGAGCAGCAGGAAGCACTATGGGCGCAGCGTCAATGACGCTGACGGTACAG
GlyAlaLeuPheLeuGlyPheLeuGlyAlaAlaGlySerThrMetGlyAlaAlaSerMetThrLeuThrValGln GCCAGAGACAATTATTGTCTGGTATAGTGCAGCAGCAGAACAATTGCTGAGGGCTATTGAGGCGCAACAGCATCTG
AlaArgGlnLeuLeuSerGlyIleValGlnGlnGlnAsnAsnLeuLeuArgAlaIleGluAlaGlnGlnHisLeu TTGCAACTCACAGTCTGGGGCATCAAGCAGCTCCAGGCAAGAATCCTGGCTGTGGAAAGATACCTAAAGGATCAA
LeuGlnLeuThrValTrpGlyIleLysGlnLeuGlnAlaArgIleLeuAlaValGluArgTyrLeuLysAspGln CAGCTCCTGGGGATTTGGGGTTGCTCTGGAAAACTCATTTGCACCACTGCTGTGCCTTGGAATGCT
GlnLeuLeuGlyIleTrpGlyCysSerGlyLysLeuIleCysThrThrAlaValProTrpAsnAla
```

FIG. 5

Nucleotide Sequence of Chimeric Protein B

```
gag-p45     AGGGCTATTGAGGGCAACAGCATCTG
         →+ ArgAlaIleGluAlaAlaGlnGlnHisLeu TTGCAACTCACAGTCTGGGCAAGCAGCTCCAGGCAAGAATCCTGGCTGTGGAAAGATACCTAAAGGATCAA
LeuGlnLeuThrValTrpGlyLysGlnLeuGlnAlaArgIleLeuAlaValGluArgTyrLeuLysAspGln CAGCTCCTGGGGATTTGGGGTTGCTCTGGAAAACTCATTTGCACCACTGCTGTGCCTTGGAATGCTAGTTGGAGT
GlnLeuLeuGlyIleTrpGlyCysSerGlyLysLeuIleCysThrThrAlaValProTrpAsnAlaSerTrpSer AATAAATCTCTGGAACAGATTTGGAATAACATGACCTGGATGGAGTGGGACAGAGAAATTACAATTACACAAGC
AsnLysSerLeuGluGlnIleIleTrpAsnAsnMetThrTrpMetGluTrpAspArgGluIleAsnAsnTyrThrSer TTAATACACTCCTTAATTGAAGAATCGCAAAACCAGCAAGAATGAACAAGAATTATTGGAATTAGATAAA
LeuIleHisSerLeuIleGluGluSerGlnAsnGlnGlnLysAsnGluGlnLeuLeuGluLeuAspLys TGGGCAAGTTTGTGG
TrpAlaSerLeuTrp
```

FIG. 6

Nucleotide Sequence of Chimeric Protein C

```
gag-p45   GGAGTAGCACCACCACCAAGGCAAAGAGAAGAGTGGTGCAGAGAGAAAAAGAGCAGTGGAATA
       → + GlyValAlaProThrLysAlaLysArgArgValValGlnArgGluLysArgAlaValGlyIle GGAGCTTTGTTCCTTGGGTTCTTGGGAGCAGCAGGAAGCACTATGGGCGCAGCGTCAATGACGCTGACGGTACAG
GlyAlaLeuPheLeuGlyPheLeuGlyAlaAlaGlySerThrMetGlyAlaAlaSerThrLeuThrValGln GCCAGACAATTATTGTCTGGTATAGTGCAGCAGCAGAACAATTGCTGAGGGCTATTGAGGCGCAACAGCATCTG
AlaArgGlnLeuLeuSerGlyIleValGlnGlnGlnAsnAsnLeuLeuArgAlaIleGluAlaGlnGlnHisLeu TTGCAACTCACAGTCTGGGGCATCAAGCAGCTCCAGGCAAGAATCCTGGCTGTGGAAAGATACCTAAAGGATCAA
LeuGlnLeuThrValTrpGlyIleLysGlnLeuGlnAlaArgIleLeuAlaValGluArgTyrLeuLysAspGln CAGCTCCTGGGGATTTGGGGTTGCTCTGGAAAACTCATTTGCACCACTGCTGTGCCTTGGAATGCTAGTTGGAGT
GlnLeuLeuGlyIleTrpGlyCysSerGlyLysLeuIleCysThrThrAlaValProTrpAsnAlaSerTrpSer AATAAATCTCTGGAACAGATTTGGAATAACATGACCTGGATGGAGTGGGACAGAGAAATTAACAATTACACAAGC
AsnLysSerLeuGluGlnIleTrpAsnAsnMetThrTrpMetGluTrpAspArgGluIleAsnAsnTyrThrSer TTAATACACTCCTTAATTGAAGAATCGCAAAACCAGCAAGAATGAACAAGAATTATTGGAATTAGATAAA
LeuIleHisSerLeuIleGluGluSerGlnAsnGlnGlnGluLysAsnGluLysGluLeuLeuGluLeuAspLys TGGGCAAGTTTGTGG
TrpAlaSerLeuTrp
```

FIG. 7

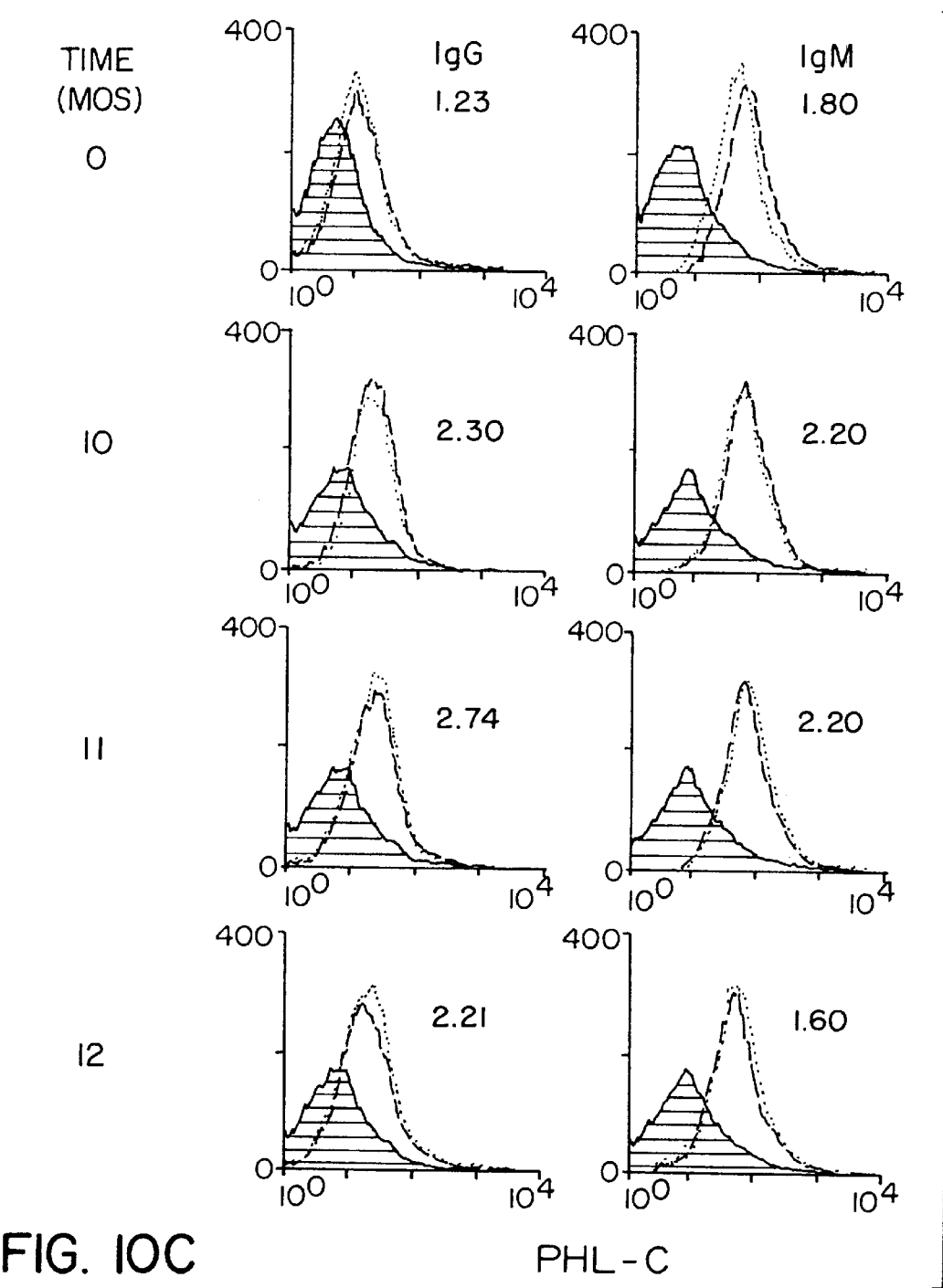
FIG. 10C  PHL-C

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
       (A) LENGTH: 1314 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

```
ATGGGTGCGA GAGCGTCAGT ATTAAGCGGG GGAGAATTAG ATCGATGGGA AAAAATTCGG      60

TTAAGGCCAG GGGGAAAGAA AAAATATAAA TTAAAACATA TAGTATGGGC AAGCAGGGAG     120

CTAGAACGAT TCGCAGTTAA TCCTGGCCTG TTAGAAACAT CAGAAGGCTG TAGACAAATA     180

CTGGGACAGC TACAACCATC CCTTCAGACA GGATCAGAAG AACTTAGATC ATTATATAAT     240

ACAGTAGCAA CCCTCTATTG TGTGCATCAA AGGATAGAGA TAAAAGACAC CAAGGAAGCT     300

TTAGACAAGA TAGAGGAAGA GCAAAACAAA AGTAAGAAAA AGCACAGCA AGCAGCAGCT      360

GACACAGGAC ACAGCAGTCA GGTCAGCCAA AATTACCCTA TAGTGCAGAA CATCCAGGGG     420

CAAATGGTAC ATCAGGCCAT ATCACCTAGA ACTTTAAATG CATGGGTAAA AGTAGTAGAA     480

GAGAAGGCTT TCAGCCCAGA AGTAATACCC ATGTTTTCAG CATTATCAGA AGGAGCCACC     540

CCACAAGATT TAAACACCAT GCTAAACACA GTGGGGGGAC ATCAAGCAGC CATGCAAATG     600

TTAAAAGAGA CCATCAATGA GGAAGCTGCA GAATGGGATA GAGTACATCC AGTGCATGCA     660

GGGCCTATTG CACCAGGCCA GATGAGAGAA CCAAGGGGA GTGACATAGC AGGAACTACT      720

AGTACCCTTC AGGAACAAAT AGGATGGATG ACAAATAATC CACCTATCCC AGTAGGAGAA     780

ATTTATAAAA GATGGATAAT CCTGGGATTA AATAAAATAG TAAGAATGTA TAGCCCTACC     840

AGCATTCTGG ACATAAGACA AGGACCAAAA GAACCTTTTA GAGACTATGT AGACCGGTTC     900

TATAAAACTC TAAGAGCCGA GCAAGCTTCA CAGGAGGTAA AAAATTGGAT GACAGAAACC     960

TTGTTGGTCC AAAATGCGAA CCCAGATTGT AAGACTATTT TAAAAGCATT GGGACCAGCG    1020

GCTACACTAG AAGAAATGAT GACAGCATGT CAGGGAGTAG GAGGACCCGG CCATAAGGCA    1080

AGAGTTTTGG CTGAAGCAAT GAGCCAAGTA ACAAATACAG CTACCATAAT GATGCAGAGA    1140

GGCAATTTTA GGAACCAAAG AAAGATGGTT AAGTGTTTCA ATTGTGGCAA AGAAGGGCAC    1200

ACAGCCAGAA ATTGCAGGGC CCCTAGGAAA AAGGGCTGTT GGAAATGTGG AAAGGAAGGA    1260

CACCAAATGA AAGATTGTAC TGAGAGACAG GCTAATTTTT TAGGGAAGAT CTAA          1314
```

(2) INFORMATION FOR SEQ ID NO:2:

(i) SEQUENCE CHARACTERISTICS:
       (A) LENGTH: 437 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

```
Met Gly Ala Arg Ala Ser Val Leu Ser Gly Gly Glu Leu Asp Arg Trp
1               5                   10                  15
```

-continued

```
Glu Lys Ile Arg Leu Arg Pro Gly Gly Lys Lys Tyr Lys Leu Lys
            20                  25                  30
His Ile Val Trp Ala Ser Arg Glu Leu Glu Arg Phe Ala Val Asn Pro
            35                  40                  45
Gly Leu Leu Glu Thr Ser Glu Gly Cys Arg Gln Ile Leu Gly Gln Leu
 50                  55                  60
Gln Pro Ser Leu Gln Thr Gly Ser Glu Glu Leu Arg Ser Leu Tyr Asn
65                   70                  75                  80
Thr Val Ala Thr Leu Tyr Cys Val His Gln Arg Ile Glu Ile Lys Asp
            85                  90                  95
Thr Lys Glu Ala Leu Asp Lys Ile Glu Glu Glu Gln Asn Lys Ser Lys
            100                 105                 110
Lys Lys Ala Gln Gln Ala Ala Ala Asp Thr Gly His Ser Asn Gln Val
            115                 120                 125
Ser Gln Asn Tyr Pro Ile Val Gln Asn Ile Gln Gly Gln Met Val His
            130                 135                 140
Gln Ala Ile Ser Pro Arg Thr Leu Asn Ala Trp Val Lys Val Val Glu
145                 150                 155                 160
Glu Lys Ala Phe Ser Pro Glu Val Ile Pro Met Phe Ser Ala Leu Ser
            165                 170                 175
Glu Gly Ala Thr Pro Gln Asp Leu Asn Thr Met Leu Asn Thr Val Gly
            180                 185                 190
Gly His Gln Ala Ala Met Gln Met Leu Lys Glu Thr Ile Asn Glu Glu
            195                 200                 205
Ala Ala Glu Trp Asp Arg Val His Pro Val His Ala Gly Pro Ile Ala
            210                 215                 220
Pro Gly Gln Met Arg Glu Pro Arg Gly Ser Asp Ile Ala Gly Thr Thr
225                 230                 235                 240
Ser Thr Leu Gln Glu Gln Ile Gly Trp Met Thr Asn Asn Pro Pro Ile
            245                 250                 255
Pro Val Gly Glu Ile Tyr Lys Arg Trp Ile Ile Leu Gly Leu Asn Lys
            260                 265                 270
Ile Val Arg Met Tyr Ser Pro Thr Ser Ile Leu Asp Ile Arg Gln Gly
            275                 280                 285
Pro Lys Glu Pro Phe Arg Asp Tyr Val Asp Arg Phe Tyr Lys Thr Leu
            290                 295                 300
Arg Ala Glu Gln Ala Ser Gln Glu Val Lys Asn Trp Met Thr Glu Thr
305                 310                 315                 320
Leu Leu Val Gln Asn Ala Asn Pro Asp Cys Lys Thr Ile Leu Lys Ala
            325                 330                 335
Leu Gly Pro Ala Ala Thr Leu Glu Glu Met Met Thr Ala Cys Gln Gly
            340                 345                 350
Val Gly Gly Pro Gly His Lys Ala Arg Val Leu Ala Glu Ala Met Ser
            355                 360                 365
Gln Val Thr Asn Ser Ala Thr Ile Met Met Gln Arg Gly Asn Phe Arg
            370                 375                 380
Asn Gln Arg Lys Ile Val Lys Cys Phe Asn Cys Gly Lys Glu Gly His
385                 390                 395                 400
Thr Ala Arg Asn Cys Arg Ala Pro Arg Lys Lys Gly Cys Trp Lys Cys
            405                 410                 415
Gly Lys Glu Gly His Gln Met Lys Asp Cys Thr Glu Arg Gln Ala Asn
            420                 425                 430
```

Phe Leu Gly Lys Ile
    435

(2) INFORMATION FOR SEQ ID NO:3:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..354

(xi) SEQUENCE DESCRIPTION: SEQ ID NO:3:

```
GGA GTA GCA CCC ACC AAG GCA AAG AGA AGA GTG GTG CAG AGA GAA AAA        48
Gly Val Ala Pro Thr Lys Ala Lys Arg Arg Val Val Gln Arg Glu Lys
 1               5                  10                  15

AGA GCA GTG GGA ATA GGA GCT TTG TTC CTT GGG TTC TTG GGA GCA GCA        96
Arg Ala Val Gly Ile Gly Ala Leu Phe Leu Gly Phe Leu Gly Ala Ala
             20                  25                  30

GGA AGC ACT ATG GGC GCA GCG TCA ATG ACG CTG ACG GTA CAG GCC AGA       144
Gly Ser Thr Met Gly Ala Ala Ser Met Thr Leu Thr Val Gln Ala Arg
         35                  40                  45

CAA TTA TTG TCT GGT ATA GTG CAG CAG CAG AAC AAT TTG CTG AGG GCT       192
Gln Leu Leu Ser Gly Ile Val Gln Gln Gln Asn Asn Leu Leu Arg Ala
     50                  55                  60

ATT GAG GCG CAA CAG CAT CTG TTG CAA CTC ACA GTC TGG GGC ATC AAG       240
Ile Glu Ala Gln Gln His Leu Leu Gln Leu Thr Val Trp Gly Ile Lys
 65                  70                  75                  80

CAG CTC CAG GCA AGA ATC CTG GCT GTG GAA AGA TAC CTA AAG GAT CAA       288
Gln Leu Gln Ala Arg Ile Leu Ala Val Glu Arg Tyr Leu Lys Asp Gln
                 85                  90                  95

CAG CTC CTG GGG ATT TGG GGT TGC TCT GGA AAA CTC ATT TGC ACC ACT       336
Gln Leu Leu Gly Ile Trp Gly Cys Ser Gly Lys Leu Ile Cys Thr Thr
            100                 105                 110

GCT GTG CCT TGG AAT GCT                                               354
Ala Val Pro Trp Asn Ala
        115
```

(2) INFORMATION FOR SEQ ID NO:4:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:4:

```
Gly Val Ala Pro Thr Lys Ala Lys Arg Arg Val Val Gln Arg Glu Lys
 1               5                  10                  15

Arg Ala Val Gly Ile Gly Ala Leu Phe Leu Gly Phe Leu Gly Ala Ala
             20                  25                  30

Gly Ser Thr Met Gly Ala Ala Ser Met Thr Leu Thr Val Gln Ala Arg
         35                  40                  45

Gln Leu Leu Ser Gly Ile Val Gln Gln Gln Asn Asn Leu Leu Arg Ala
     50                  55                  60

Ile Glu Ala Gln Gln His Leu Leu Gln Leu Thr Val Trp Gly Ile Lys
 65                  70                  75                  80
```

```
Gln Leu Gln Ala Arg Ile Leu Ala Val Glu Arg Tyr Leu Lys Asp Gln
            85                  90                  95

Gln Leu Leu Gly Ile Trp Gly Cys Ser Gly Lys Leu Ile Cys Thr Thr
            100                 105                 110

Ala Val Pro Trp Asn Ala
        115

(2) INFORMATION FOR SEQ ID NO:5:

(i) SEQUENCE CHARACTERISTICS:
        (A) LENGTH: 342 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..342

(xi) SEQUENCE DESCRIPTION: SEQ ID NO:5:

AGG GCT ATT GAG GCG CAA CAG CAT CTG TTG CAA CTC ACA GTC TGG GGC         48
Arg Ala Ile Glu Ala Gln Gln His Leu Leu Gln Leu Thr Val Trp Gly
  1               5                  10                  15

ATC AAG CAG CTC CAG GCA AGA ATC CTG GCT GTG GAA AGA TAC CTA AAG         96
Ile Lys Gln Leu Gln Ala Arg Ile Leu Ala Val Glu Arg Tyr Leu Lys
                20                  25                  30

GAT CAA CAG CTC CTG GGG ATT TGG GGT TGC TCT GGA AAA CTC ATT TGC        144
Asp Gln Gln Leu Leu Gly Ile Trp Gly Cys Ser Gly Lys Leu Ile Cys
            35                  40                  45

ACC ACT GCT GTG CCT TGG AAT GCT AGT TGG AGT AAT AAA TCT CTG GAA        192
Thr Thr Ala Val Pro Trp Asn Ala Ser Trp Ser Asn Lys Ser Leu Glu
        50                  55                  60

CAG ATT TGG AAT AAC ATG ACC TGG ATG GAG TGG GAC AGA GAA ATT AAC        240
Gln Ile Trp Asn Asn Met Thr Trp Met Glu Trp Asp Arg Glu Ile Asn
 65                 70                  75                  80

AAT TAC ACA AGC TTA ATA CAC TCC TTA ATT GAA GAA TCG CAA AAC CAG        288
Asn Tyr Thr Ser Leu Ile His Ser Leu Ile Glu Glu Ser Gln Asn Gln
                85                  90                  95

CAA GAA AAG AAT GAA CAA GAA TTA TTG GAA TTA GAT AAA TGG GCA AGT        336
Gln Glu Lys Asn Glu Gln Glu Leu Leu Glu Leu Asp Lys Trp Ala Ser
            100                 105                 110

TTG TGG                                                                 342
Leu Trp (2) INFORMATION FOR SEQ ID NO:6:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO:6:

Arg Ala Ile Glu Ala Gln Gln His Leu Leu Gln Leu Thr Val Trp Gly
  1               5                  10                  15

Ile Lys Gln Leu Gln Ala Arg Ile Leu Ala Val Glu Arg Tyr Leu Lys
                20                  25                  30

Asp Gln Gln Leu Leu Gly Ile Trp Gly Cys Ser Gly Lys Leu Ile Cys
            35                  40                  45

Thr Thr Ala Val Pro Trp Asn Ala Ser Trp Ser Asn Lys Ser Leu Glu
```

```
            50                   55                    60
Gln Ile Trp Asn Asn Met Thr Trp Met Glu Trp Asp Arg Glu Ile Asn
 65                     70                   75                   80

Asn Tyr Thr Ser Leu Ile His Ser Leu Ile Glu Glu Ser Gln Asn Gln
                    85                   90                   95

Gln Glu Lys Asn Glu Gln Glu Leu Leu Glu Leu Asp Lys Trp Ala Ser
                100                 105                 110

Leu Trp (2) INFORMATION FOR SEQ ID NO:7:

(i) SEQUENCE CHARACTERISTICS:
        (A) LENGTH: 528 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..528

(xi) SEQUENCE DESCRIPTION: SEQ ID NO:7:

GGA GTA GCA CCC ACC AAG GCA AAG AGA AGA GTG GTG CAG AGA GAA AAA          48
Gly Val Ala Pro Thr Lys Ala Lys Arg Arg Val Val Gln Arg Glu Lys
  1               5                  10                  15

AGA GCA GTG GGA ATA GGA GCT TTG TTC CTT GGG TTC TTG GGA GCA GCA          96
Arg Ala Val Gly Ile Gly Ala Leu Phe Leu Gly Phe Leu Gly Ala Ala
             20                  25                  30

GGA AGC ACT ATG GGC GCA GCG TCA ATG ACG CTG ACG GTA CAG GCC AGA         144
Gly Ser Thr Met Gly Ala Ala Ser Met Thr Leu Thr Val Gln Ala Arg
         35                  40                  45

CAA TTA TTG TCT GGT ATA GTG CAG CAG CAG AAC AAT TTG CTG AGG GCT         192
Gln Leu Leu Ser Gly Ile Val Gln Gln Gln Asn Asn Leu Leu Arg Ala
     50                  55                  60

ATT GAG GCG CAA CAG CAT CTG TTG CAA CTC ACA GTC TGG GGC ATC AAG         240
Ile Glu Ala Gln Gln His Leu Leu Gln Leu Thr Val Trp Gly Ile Lys
 65                  70                  75                  80

CAG CTC CAG GCA AGA ATC CTG GCT GTG GAA AGA TAC CTA AAG GAT CAA         288
Gln Leu Gln Ala Arg Ile Leu Ala Val Glu Arg Tyr Leu Lys Asp Gln
                 85                  90                  95

CAG CTC CTG GGG ATT TGG GGT TGC TCT GGA AAA CTC ATT TGC ACC ACT         336
Gln Leu Leu Gly Ile Trp Gly Cys Ser Gly Lys Leu Ile Cys Thr Thr
            100                 105                 110

GCT GTG CCT TGG AAT GCT AGT TGG AGT AAT AAA TCT CTG GAA CAG ATT         384
Ala Val Pro Trp Asn Ala Ser Trp Ser Asn Lys Ser Leu Glu Gln Ile
        115                 120                 125

TGG AAT AAC ATG ACC TGG ATG GAG TGG GAC AGA GAA ATT AAC AAT TAC         432
Trp Asn Asn Met Thr Trp Met Glu Trp Asp Arg Glu Ile Asn Asn Tyr
    130                 135                 140

ACA AGC TTA ATA CAC TCC TTA ATT GAA GAA TCG CAA AAC CAG CAA GAA         480
Thr Ser Leu Ile His Ser Leu Ile Glu Glu Ser Gln Asn Gln Gln Glu
145                 150                 155                 160

AAG AAT GAA CAA GAA TTA TTG GAA TTA GAT AAA TGG GCA AGT TTG TGG         528
Lys Asn Glu Gln Glu Leu Leu Glu Leu Asp Lys Trp Ala Ser Leu Trp
                165                 170                 175

(2) INFORMATION FOR SEQ ID NO:8:

(i) SEQUENCE CHARACTERISTICS:
        (A) LENGTH: 176 amino acids
```

(B) TYPE: amino acid
        (D) TOPOLOGY: linear (ii) MOLECULE TYPE: protein (xi) SEQUENCE DESCRIPTION: SEQ ID NO:8:

Gly Val Ala Pro Thr Lys Ala Lys Arg Arg Val Val Gln Arg Glu Lys
 1               5                  10                  15

Arg Ala Val Gly Ile Gly Ala Leu Phe Leu Gly Phe Leu Gly Ala Ala
                20                  25                  30

Gly Ser Thr Met Gly Ala Ala Ser Met Thr Leu Thr Val Gln Ala Arg
            35                  40                  45

Gln Leu Leu Ser Gly Ile Val Gln Gln Gln Asn Asn Leu Leu Arg Ala
        50                  55                  60

Ile Glu Ala Gln Gln His Leu Leu Gln Leu Thr Val Trp Gly Ile Lys
 65                  70                  75                  80

Gln Leu Gln Ala Arg Ile Leu Ala Val Glu Arg Tyr Leu Lys Asp Gln
                85                  90                  95

Gln Leu Leu Gly Ile Trp Gly Cys Ser Gly Lys Leu Ile Cys Thr Thr
            100                 105                 110

Ala Val Pro Trp Asn Ala Ser Trp Ser Asn Lys Ser Leu Glu Gln Ile
        115                 120                 125

Trp Asn Asn Met Thr Trp Met Glu Trp Asp Arg Glu Ile Asn Asn Tyr
130                 135                 140

Thr Ser Leu Ile His Ser Leu Ile Glu Glu Ser Gln Asn Gln Gln Glu
145                 150                 155                 160

Lys Asn Glu Gln Glu Leu Leu Glu Leu Asp Lys Trp Ala Ser Leu Trp
                165                 170                 175

(2) INFORMATION FOR SEQ ID NO:9:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GATCCATGGG TGCGAGAGCG TCAGTATTAA GCGGGGGAGA ATTAGAT                47

(2) INFORMATION FOR SEQ ID NO:10:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CGATCTAATT CTCCCCCGCT TAATACTGAC GCTCTCGCAC CCATG                  45

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GATCTCTAAG GATCCTTA                                                       18

(2) INFORMATION FOR SEQ ID NO:12:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

GATCTAAGGA TCCTTAGA                                                       18

(2) INFORMATION FOR SEQ ID NO:13:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

CAGATCTCCG GAGTAGCACC CACC                                                24

(2) INFORMATION FOR SEQ ID NO:14:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

GAGATCTGTT AAGCATTCCA AGGCAC                                              26

(2) INFORMATION FOR SEQ ID NO:15:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:15:

CTCGAAGATC TCCAGGGCTA TTGAGGCGCA                                          30

(2) INFORMATION FOR SEQ ID NO:16:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:16:

```
CTCGAAGATC TATTACCACA AACTTGCCCA                                   30
```

(2) INFORMATION FOR SEQ ID NO:17:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
CGCTGATCAA TGAGAGTGHA GGAGAAATAT CAGC                              34
```

(2) INFORMATION FOR SEQ ID NO:18:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
CGCTGATCAT TATAGCAAAA TCCTTTCCAA GCCC                              34
```

(2) INFORMATION FOR SEQ ID NO:19:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (xi) SEQUENCE DESCRIPTION: SEQ ID NO:19:

```
GGAGTAGCAC CCACCAAGGC AAAGAGAAGA GTGGTGCAGA GAGAAAAAAG AGCAGTGGGA   60
ATAGGAGCTT TGTTCCTTGG GTTCTTGGGA GCAGCAGGAA GCACTATGGG CGCAGCGTCA  120
ATGACGCTGA CGGTACAGGC CAGACAATTA TTGTCTGGTA TAGTGCAGCA GCAGAACAAT  180
TTGCTGAGGG CTATTGAGGC GCAACAGCAT CTGTTGCAAC TCACAGTCTG GGGCATCAAG  240
CAGCTCCAGG CAAGAATCCT GGCTGTGGAA AGATACCTAA AGGATCAACA GCTCCTGGGG  300
ATTTGGGGTT GCTCTGGAAA ACTCATTTGC ACCACTGCTG TGCCTTGGAA TGCTTAA     357
```

(2) INFORMATION FOR SEQ ID NO:20:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

```
AGGGCTATTG AGGCGCAACA GCATCTGTTG CAACTCACAG TCTGGGGCAT CAAGCAGCTC   60
CAGGCAAGAA TCCTGGCTGT GGAAAGATAC CTAAAGGATC AACAGCTCCT GGGGATTTGG  120
GGTTGCTCTG GAAAACTCAT TTGCACCACT GCTGTGCCTT GGAATGCTAG TTGGAGTAAT  180
AAATCTCTGG AACAGATTTG GAATAACATG ACCTGGATGG AGTGGGACAG AGAAATTAAC  240
AATTACACAA GCTTAATACA CTCCTTAATT GAAGAATCGC AAAACCAGCA AGAAAAGAAT  300
GAACAAGAAT TATTGGAATT AGATAAATGG GCAAGTTTGT GGTAA                 345
```

(2) INFORMATION FOR SEQ ID NO:21:

(i) SEQUENCE CHARACTERISTICS:
        (A) LENGTH: 531 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
GGAGTAGCAC CCACCAAGGC AAAGAGAAGA GTGGTGCAGA GAGAAAAAAG AGCAGTGGGA      60

ATAGGAGCTT TGTTCCTTGG GTTCTTGGGA GCAGCAGGAA GCACTATGGG CGCAGCGTCA     120

ATGACGCTGA CGGTACAGGC CAGACAATTA TTGTCTGGTA TAGTGCAGCA GCAGAACAAT     180

TTGCTGAGGG CTATTGAGGC GCAACAGCAT CTGTTGCAAC TCACAGTCTG GGGCATCAAG     240

CAGCTCCAGG CAAGAATCCT GGCTGTGGAA AGATACCTAA AGGATCAACA GCTCCTGGGG     300

ATTTGGGGTT GCTCTGGAAA ACTCATTTGC ACCACTGCTG TGCCTTGGAA TGCTAGTTGG     360

AGTAATAAAT CTCTGGAACA GATTTGGAAT AACATGACCT GGATGGAGTG GGACAGAGAA     420

ATTAACAATT ACACAAGCTT AATACACTCC TTAATTGAAG AATCGCAAAA CCAGCAAGAA     480

AAGAATGAAC AAGAATTATT GGAATTAGAT AAATGGGCAA GTTTGTGGTA A              531
```

IMMUNOFLUORESCENCE ASSAY FOR THE DETECTION OF ANTIBODIES USING RECOMBINANT ANTIGENS IN INSOLUBLE FORM

CROSS-REFERENCE TO RELATED APPLICATION

This application is a continuation-in-part of U.S. application Ser. No. 08/164,789, filed Dec. 10, 1993, now abandoned the content of which is entirely incorporated herein by reference.

FIELD OF THE INVENTION

The present invention relates to an assay for the detection of various disease states which utilizes antigens in insoluble form and more particularly, for the detection of HIV infection. The assay of the present invention has a high sensitivity allowing for detection of antibodies to the HIV virus in the "window" period.

BACKGROUND OF THE INVENTION

Enzyme immunoassays (EIA) and Western Blot assays (WB) have been routinely used for detecting HIV infection for several years. The implementation of these tests has significantly reduced the risk of transfusion-related HIV infection. However, some recent studies based on the detection of HIV DNA have demonstrated that some HIV infected individuals do not have any detectable amount of anti-HIV antibodies when the approved tests are performed. Data from several studies indicate that there is a "window period" estimated to span from a few weeks to several months or even several years between initial HIV infection and seroconversion. Cases of post-transfusion HIV infection have been reported from seronegative blood donors. This is assumed to be a consequence of donation during the "window" period on the part of these donors.

To verify the presence of HIV-antibody in donors of reactive samples to EIA, the Western Blot assay has been used for confirmatory testings (Ulstrup, J. C. et al, Lancet i:1151–1152). In this assay, 6 to 9 characteristic bands indicating antibodies to HIV surface and core antigens are observed if antibodies to HIV-1 proteins are present (positive), and no bands if antibodies are absent (negative). However, a significant proportion of EIA repeatedly reactive samples react only to the HIV-1 gag-derived core proteins (p17, p24 and p55) on the WB test (Kleinman, S., 1990, Arch. Pathol. Lab. Med. 114:298–303, Tribe D. E. et al, 1988, J. Clin. Microbiol. 26:641–647). This reactivity does not meet the definition of HIV-1 positive or negative in the criteria for WB tests and as a result these samples are labelled as HIV-1 WB indeterminates. Studies have established that 30 to 40 percent of EIA repeatedly positive donors are HIV-1 WB indeterminates, a figure that is typical in North America. Follow-up studies performed in regions of high prevalence of HIV show that while 95 to 99 percent of these are not infected with HIV, the remaining 1 to 5 percent of blood donors with HIV-1 WB indeterminate results are true seroconverters, usually at an early stage of infection (Busch, M. P. et al., 1991, Transfusion 31:129–137; Gallo D. et al, 1986, J. Clin. Microbiol. 23:1049–1051). In order to optimize the safety of transfusion, all donors with HIV-1 WB indeterminate results are deferred. The majority of donors with HIV-1 WB indeterminate results undergo needless anxiety, their deferral represents a significant loss of donors and recipients are still worried about contamination of blood taken from "window" period of seroconversion donors. A highly sensitive assay is thus also desirable in order to properly classify these indeterminate results.

Partially purified disrupted virus is used as an antigen for most currently licensed screening and confirmatory tests. Human cells are always used for culturing the HIV-1 virus (Dodd, R. Y. and C. T. Fang, 1990, Arch. Pathol. Lab. Med. 114:240–245). Recombinant proteins and synthetic peptides have been recently licensed for screening tests (Busch M. P. et al., 1991, Transfusion 31:129–137; Das P.C. et al., 1992, Trans Med 2:249–250; Ramirez E. P., 1992, J. Clin. Microbiol. 30:801–805). In theory, these antigens can provide more sensitive and definitive assays. However, most recombinant proteins are produced in $E.\ coli$ and denatured during the purification and processing of the antigens. Also, a certain proportion of donors still show cross-reactivity to HIV core antigens (such as antigen p24), and sensitivity is limited to detecting very early HIV antibodies.

A serious drawback to the use of synthetic peptides is related to the fact that in some HIV-1 infected patients and seroconverters in high risk populations, the serum antibody titre is very low, or undetectable, either because of complex formation between p24 and antibodies or the loss of specific clones of antibody producing cells (Orsknov, L. B., Eur. J. Clin. Microbiol. Inf. Dis. 8:614). Synthetic peptides, which in general only cover one or two epitopes, do not efficiently detect such low titre antibodies and furthermore have a limited ability to take on the natural three dimensional structures of antigen.

An immunofluorescence assay (IFA) has recently been licensed as an alternate confirmatory test for detecting HIV-1 antibodies (FDA Memorandum, 1992, Summer:56–67). IFA is rapid, simple and inexpensive. However, it is a subjective procedure requiring well trained personnel (Ascher, M. S. 1990, Arch. Pathol. Lab. Med. 114:246–248). This is a limitation for users and false positive and false negative results still occur in the IFA tests because of cross-reactivity of some antibodies to antigens on the human cells in which the HIV virus is cultured. Fixing of the infected cells before incubation also has been shown to lead to false positive and negative results (McHugh, T. M., 1986, Diagnos. Immunol. 4:233–240).

An assay based on immunofluorescence was recently developed to detect antibodies to HIV-1 by using flow cytometry (FIFA) (Sligh, J. M., 1989, Am. J. Clin. Path. 91:210–214). FIFA is a sensitive, quantitative test. In a typical FIFA protocol, HIV-1 infected cells are used directly for the test. However, false positive and false negative results may occur because of the HIV-1 antibody cross-reactivity to the antigens (such as HLA) on human cells in which the virus is cultured and used as antigens in FIFA. Another concern is with biohazards caused by the infectious virus which is a big limitation for users. Fixing the HIV-1 infected cells for inactivation of the virus before incubation has shown to lead to higher cross reactivity on the cells.

The present invention is directed to a flow cytometric immunofluorescence assay (r-FIFA) using insoluble forms of recombinant proteins expressed in an expression system such as the baculovirus system. In a preferred embodiment, r-FIFA is used for the detection of the HIV virus infection. Insoluble forms of recombinant HIV-1 proteins such as HIV-1 gag p45 protein, gag gp-41 chimeric proteins, HIV-1 precursor polyproteins pol 97 and gp160 are used as autologous carriers (in place of beads) and antigens to detect HIV-1 antibodies using flow cytometry. The baculovirus expression system has become a major recombinant protein production system because of several advantages over bacterial and mammalian systems including superior yield of recombinant protein, safety (baculovirus is not infectious to humans) and fidelity of its products.

In sensitivity comparison between r-FIFA and currently licensed tests, r-FIFA was found to be more sensitive, the average increase in sensivity for early detection of HIV-1 infection being greater than 20 days. r-FIFA has permitted the detection and quantification of HIV-1 specific IgG, IgM and IgA antibodies during the window period. The use of HIV-1 recombinant proteins in an immunofluorescence assay (r-FIFA) solves the problems of antibody cross-reactivity to antigen on human cells and the biohazard concern with the original FIFA.

SUMMARY OF THE INVENTION

In a broad embodiment, the invention relates to the use of an insoluble form of at least one recombinant protein as a carrier and antigen in a flow cytometric immunofluorescence assay for the detection of a disease state wherein said protein reacts with an antibody present in said disease state. In a preferred embodiment, the invention relates to the use of an insoluble form of at least one recombinant protein as a carrier and antigen in a flow cytometric immunofluorescence assay for the detection of HIV.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

The invention will be better understood through the following detailed description of the preferred embodiment in conjunction with the accompanying drawings in which:

FIGS. 1A–1C represent the construction of a recombinant baculovirus containing the HIV-1 gag gene sequence coding for gag-45 protein. The gag-45 coding region was isolated from the plasmid pHxB-2D (8). FIG. 1A; a Cla1-Bgl II fragment was modified and subcloned into pUC19 by ligation with two synthetic oligonucleotide linkers. FIG. 1B; the linker 1 (SEQ ID NOS:9 and 10) contains a Bam H1 site and the missing sequence including the translation initiation codon (ATG) at N-terminal of gag gene. The linker 2 (SEQ ID NOS:11 and 12) creates a translation termination codon (TAA) followed by a Bam H1 site. FIG. 1C; the Bam H1 fragment was isolated from the pUC19-gag45 and inserted into the Bam H1 site of transfer vector pAcYM1 (9). The recombinant transfer vector pAcYM1-gag 45 was used for co-transfection of SF9 cells with wild type AcNpV DNA and then the recombinant baculovirus gag45 gene was isolated to express the recombinant protein gag45;

FIGS. 2A and 2B show the nucleotide sequence of HIV-1 gag protein p45 (SEQ ID NO:1);

FIG. 3 is the amino acid sequence of HIV-1 gag protein p-45 (SEQ ID NO:2);

FIG. 5 is the nucleotide sequence (SEQ ID NO:3) and amino acid sequence of chimeric protein A (SEQ ID NO:4);

FIG. 6 is the nucleotide sequence (SEQ ID NO:5) and amino acid sequence of chimeric protein B (SEQ ID NO:6);

FIG. 7 is the nucleotide sequence (SEQ ID NO:7) and amino acid sequence of chimeric protein C (SEQ ID NO:8); FIG. 8A: a flow cytometric histograms of the seropositive and seronegative plasma are presented showing HIV-1 specific antibody (IgG) positive signal (the line peaks) and the negative signal (solid peak). Each of the two line peaks represent the duplicates of the assay. The heavy overlapping of the duplicates indicates the high reproducibility of r-FIFA. FIG. 8B: The median fluorescence intensity of the HIV-1 positive sample (○) and the negative sample were plotted (●) over the dilutions (1:25 to 1:25 600). The median fluorescence intensity ratio of HIV-1 positive sample to HIV-1 negative sample (S/N) is highest at 1:25. C: The dilution of 1:25 was chosen for r-FIFA to detect IgG (FIG. 8C) and IgM (FIG. 8D) antibodies (B-IgG and B-IgM) to HIV-1 in a HIV-1 positive sample by double staining with goat anti-human IgG FITC and IgM R-PE;

FIGS. 10A–10C represent detection of early HIV-1 antibodies (IgG and IgM) using r-FIFA in the samples from three individuals (PHL-A, (FIG. 10A), PHL-B, (FIG. 10B), PHL-C (FIG. 10C) who were infected but seronegative in the first bleed (upper row) by recently licensed screening tests. The numbers under IgG and IgM indicate the s/c value of the samples; 1.0 or greater is considered positive;

FIG. 13A: the sample tested had weak antibodies to HIV-1 core (45) and strong antibodies to gag-gp41 (cc) by Western Blot (IgG only).

FIG. 13B: the antigen gag-p45 (45) and antigen gag-gp41 (cc,B) were visualized by Coomassie blue staining of the polyacrylamide gel. The r-FIFA results (FIGS. 13A and 13B) are shown to be concordant with Western Blot results;

FIGS. 14A–14C represent data obtained from FIGS. 11C, 11A and 11G, respectively.

DESCRIPTION OF THE PREFERRED EMBODIMENT

The present invention relates to the use of an insoluble recombinant protein in a flow cytometric immunofluorescence assay, hereinafter referred to as r-FIFA, for the detection of antibodies. In the examples that follow, the use of insoluble forms of the HIV-1 gag precursor p55, termed p45 protein, which includes p17, p24 and part of p16 and chimeric particles of gag-gp41 fusion proteins; the gp160 and pol97 proteins for the early detection of HIV as well as the hepatitis B core antigen for the detection of hepatitis B is described.

Recombinant proteins for the present invention are prepared in the baculovirus expression system since the baculovirus expression system has several advantages over bacterial and mammalian systems. These include a superior yield of recombinant protein, safety and fidelity of the products. Glycosylation, myristolyation, proteolytic processing and other post-translational modifications that occur in baculovirus expressed proteins are similar or identical to the native HIV-1 proteins and to HIV-1 proteins derived from mammalian cell culture systems.

When expressed in insect cells, baculovirus encoded rp45 exhibits two molecular forms, an insoluble particle form and a soluble protein. The particle form of gag protein consists of a membrane-enveloped corelike particle released into the medium by budding at the plasma membrane. Both of the two forms of gag rp45 are myristoylated (Mervis, R. J., 1988, J. Virol. 62:3993–4002). HIV-1 gag particle is 100 to 120 nm in diameter. It is a good carrier for inserting immunoreactive domains of other proteins, such as neutralizing epitopes of gp120 by using recombinant DNA techniques, thereby extending the immunoreactivity spectrum of this gag protein.

Standard performance panels obtained from BBI (Boston Biomedica Inc.) were used for the evaluation of r-FIFA. These performance panels are made available to enable manufacturers and users to test and assess their anti-HIV-1 test systems, especially with regard to specificity, reproducibility and sensitivity. BBI provides comprehensive data for comparative analysis. Each set of BBI panels includes 6 to 14 aliquots assembled from a repository of frozen sera or plasma units. An anti-HIV-1 low titer performance panel (PRB-104), anti-HIV-1 seroconversion panels D(PRB 904), E(PRB 905), H(PRB-908), J(PRB 910), K(PRB-911), P(PRB-916), Q(PRB-917), R(PRB-918) and three HIV-1 seroconversion specimens provided by PHL were tested and analyzed by r-FIFA. To confirm the specificity of r-FIFA, 295 plasma or serum samples from random blood donors, 105 Western Blot positive samples and 138 E1A reactive, Western Blot indeterminate samples from The Canadian Red Cross Society, National Testing Laboratory were also tested.

EXAMPLE 1

Figure 1C:
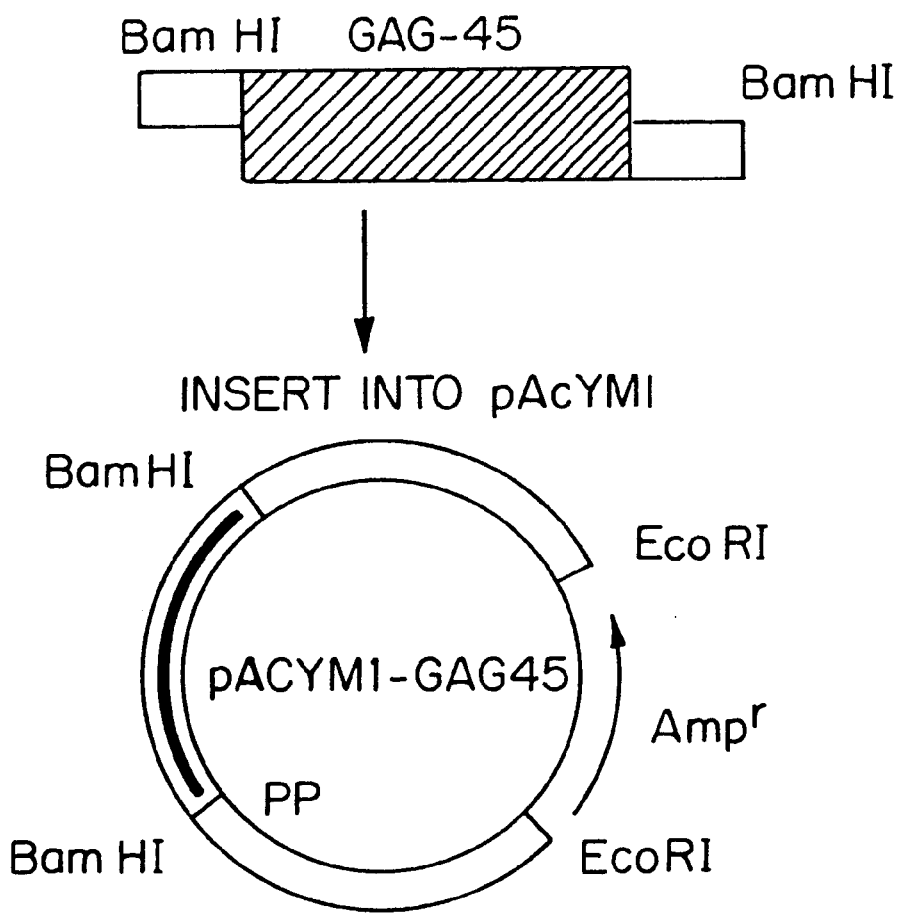

Construction of Recombinant Baculoviruses for the Expression of HIV-1 Gag p45 and Chimeric gag-gp41 Proteins Recombinant baculoviruses were constructed to express HIV-1 gag p45 and chimeric gag-gp41 proteins gag-gp41 A, gag-gp41 B and gag-gp41 C. The gag p45 coding region (including intact p17, p24 and part of p16 coding sequences) was isolated from the plasmid pHxB-2D (Ratner et al., 1985, Nature 313, 277–284). A ClaI-BgI II fragment was modified and subcloned into pUC19 by using synthetic oligonucleotide linkers. Linker 1 contains a Bam H1 site and the missing sequence including the translation initiation codon (ATG) at the N-terminal of the gag gene. Linker 2 created a translation termination codon (TAA) followed by a Bam H1 site. The Bam H1 fragment was isolated from pUC19-gag p45 and inserted into the Bam H1 site of transfer vector pAcYM1 as illustrated in FIG. 1. The recombinant plasmid pAcYM1-gag p45 was used for co-transfection of SF9 cells with wild type AcNPV DNA and then the recombinant baculovirus gag-p45 was isolated to express the recombinant protein gag p45. Three gag-gp41 chimeric proteins were constructed and are referred to as gag-gp41 A, gag-gp41 B and gag-gp41 C and represented in schematic form in FIG. 4. The gag coding sequence in the three constructions is the same as gag p45. The gp41 coding sequences A (nucleotides 7737–8090, 118 a.a.), B (nucleotides 7923–8264, 114 a.a), and C (nucleotides 7737–8264 176 a.a.) were inserted respectively at the Bgl II site at the end of the gag-p45 gene. The nucleotide and amino acid sequences of gag-p45 (SEQ ID:1 A and SEQ ID:2 respectively) are provided in FIGS. 2 and 3. The nucleotide and amino acid sequences of the three chimeric proteins are provided in FIGS. 5, 6 and 7 (SEQ ID:3 and 4 for Protein A, SEQ ID:5 and 6 for protein B and SEQ ID:7 and 8 for protein C). The chimeric DNAs were isolated and inserted into the Bam H1 cloning site of transfer vector plasmid pVL 1393 and cotransfection was performed using the BaculoGold system (Pharminogen). Recombinant viruses were isolated as chimeric gag-gp41 A, gag-gp41 B and gag-gp41 C.

Construction of Recombinant HIV-1 Gag/Env Chimeric Proteins

Figure 4:
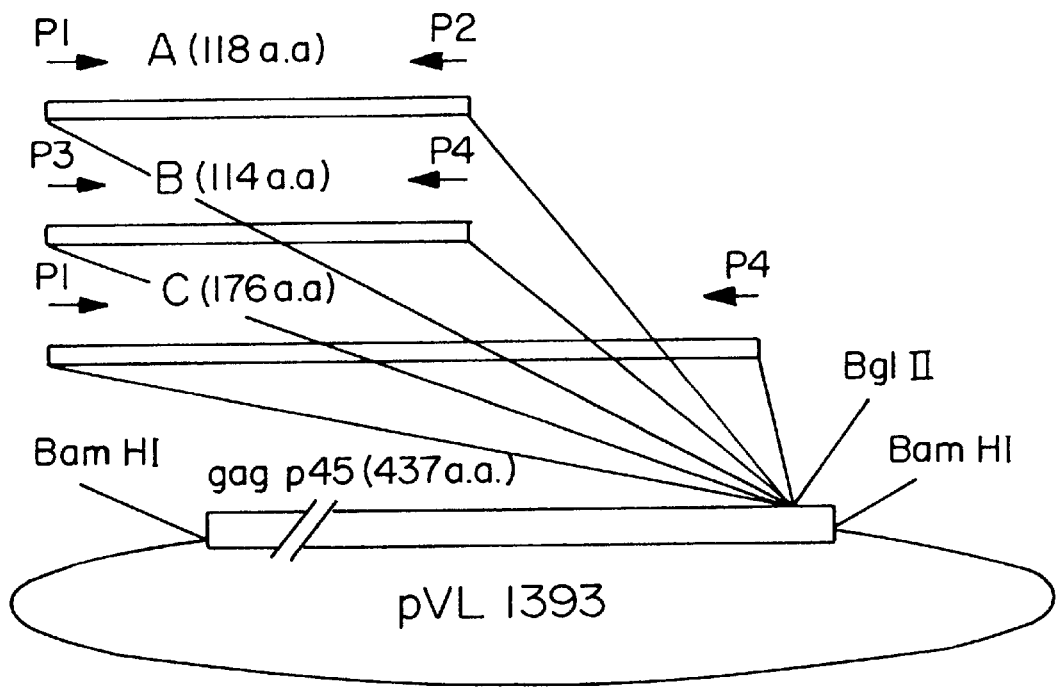
FIG. 4 is a schematic representation of the construction of recombinant HIV-1 gag gp41 proteins. Three gag-gp 41 chimeric proteins were constructed based on the truncated gag precursor p45 gene sequence. The gp41 coding region A (nucleotides 7737–8090), 118 a.a.), B (nucleotides 7923–8264, 114 a.a.) and C (nucleotides 7737–8264, 176 a.a.) were amplified by PCR with primers $P_1$ (SEQ ID NO:13), $P_2$ (SEQ ID NO:14), $p_3$ (SEQ ID NO:15) and $p_4$ (SEQ ID NO:16) which contain a Bgl II enzyme site at both ends and a stop codon TAA at the 3' end and then inserted respectively into the Bgl II enzyme site at 3' end of gag-p45 coding sequence in the recombinant plasmid pAcYm1 gag p45. The chimeric DNAs were isolated and inserted into the Bam H1 cloning site of AcNPV transfer vector plasmid pVL 1393. The recombinant viruses gag-gp 41A, gag-gp 41B and gag-gp 41C were isolated and purified after co-transfection.

Three gag/env chimeric proteins were constructed and were referred to as chimeric A, B, and C as shown in FIG. 4. The gag DNA sequence in the three proteins was the same. That sequence contained a 5' truncated HIV-1 gag protein (p45) sequence excluding the TAA termination codon. In addition, chimeric A contained 118 a.a. env sequences (nucleotides 7737–8090 SEQ ID:3). Chimeric B contained 114 a.a. env sequences (nucleotides 7923–8264 SEQ ID:5) and chimeric C contained 176 a.a. env sequences (nucleotides 7737–8264 SEQ ID:7). The chimeric DNA was inserted into the Bam H1 restriction site of plasmid pVL1393 and cotransfection was performed using the BaculoGold transfection system. The nucleotide sequences of the three chimeric proteins are provided in FIGS. 5, 6 and 7.

a) Amplification of HIV-1 env Regions

About 100 ng of HIV-1 plasmid DNA (pHxB-20) was used in the polymerase chain reaction (PCR). Amplification was performed using primers p1 and p2 to amplify the env region of chimeric A. Primers p3 and p4 were used to amplify the env region of chimeric B and primers p1 and p4 were used to amplify the env region of chimeric C as shown in FIG. 4. PCR was performed using the Perkin Elmer Cetus amplification kit and their cycler (Gene A mp PCR System 9600). The amplification reaction was denatured by heating to 95° C. for 20 seconds, then annealed at 68° C. for 15 seconds and extended at 72° for 45 seconds. A total of 30 cycles were performed.

b) Cloning and Bgl II Digestion

The PCR product of each of the env sequences was inserted into the TA cloning vector using the manufacturer's procedures (TA cloning kit, Invitrogen). Using the same kit, transformation of *E. coli* competent cells was performed and recombinant white colonies were picked up and grown in LB medium. DNA was extracted from the cells using published procedures and was used for digestion. This DNA was digested to completion with Bgl II (Gibco BRL), which incises twice in the plasmid at each of the two primers and hence releases the PCR product and introduces Bgl II sticky ends. This DNA was then ligated to the Bgl II cut pAcyM1 (at position 1310 nucleotides) vector, which contains the truncated HIV-1 gag DNA sequence. The ligated DNA was then introduced into *E. coli* competent cells and recombinant white colonies were grown in LB media. This DNA was extracted and used for Bam H1 digestion.

c) Barn H1 Digestion and Cloning Into pVL1393

The plasmid pAcYM 1, which contained the recombinant gag/env sequences, was digested with Bam H1 (Gibco BRL) in order to release the entire insert. This DNA was then ligated to Bam H1 cut pVL1393 (BaculoGold transfection vector). After ligation and transformation of *E. coli* competent cells, white colonies were grown in LB and DNA was extracted and purified.

d) Cotransfection

An equivalent of 5 μg of recombinant pVL1393 was used in the cotransfection procedure. This procedure was performed as recommended by the manufacturer (BaculoGold transfection kit, Pharminogen).

It will be understood by a person skilled in the art that while the present application only describes the preparation of three chimeric proteins, other chimeric proteins could be made and used as well in the immunofluorescence assay. Chimeric proteins containing conservative regions and having at least an antigenic or immunoreactive domain or epitope could also be used for the present invention.

EXAMPLE 2

Construction of Recombinant Baculovirus to Express HIV-1 gp160

A 5' end primer and 3' end primer having the following sequences:

```
5'end primer                               (SEQ ID NO: 17)
CGC TGA TCA ATG AGA GTG HAG GAG AAA TAT CAG C 3'end primer                               (SEQ ID NO: 18)
CGC TGA TCA TTA TAG CAA AAT CCT TTC CAA GCC C
``` were designed to amplify the entire HIV-1 gp160 coding sequence (env open reading frame) (Ratner et al., Nature 313, 277–284) by polymerase chain reaction (PCR). In addition, a BcL1 enzyme recognition sequence was included in each of the primers to facilitate cloning of the coding sequence into a vector plasmid. After the gp160 gene was cloned and inserted into a baculovirus transfer vector pvl 1393, by techniques well known in the art, the co-transfection was performed using the procedure provided by the Baculo-Gold System (Pharmigen). The recombinant virus was isolated to express a fully glycosylated gp160 polyprotein, the precursor of HIV-1 env gene products.

EXAMPLE 3

Construction of Recombinant Baculovirus to Express HIV-1 pol 97

The recombinant virus expressing pol 97 was constructed as disclosed in Hu et al., 1991, Proc. Natl. Acad. Sci., 88, 4596–4600.

EXAMPLE 4

SF9 Cell Culture and HIV Recombinant Protein Production

Spodoptera frugiperda (Sf9) cells are grown in monolayer (175 cm² Falcon tissue culture flasks) or roller bottle (850 cm² cell culture bottles) cultures. The medium used for either culture condition is Gibco BRL Sf900 medium supplemented with 100 U/ml each of sodium penicillin G and streptomycin sulphate (Gibco BRL) or Sigma TNM-FH medium supplemented with 10% (v/v) fetal bovine serum (Gibco BRL) and 100 U/ml each of the above antibiotics.

The cells are infected at an moi of 5–10 with recombinant baculovirus (*Autographa californica*). Harvest of the intracellular protein (protein contained within the cells prior to cell lysis) was done using the same procedure for both the monolayer and roller bottle cultures after an optimum time of 72 hours post infection. The cells were released from the surface of the flask or bottle and the suspension was spun down for 10 minutes at 250×g at ambient temperature on a Beckman GP centrifuge. The cell pellet and the supernatant were then further processed. The supernatant (extracelluar protein) was transferred to Beckman Ultraclear tubes and spun down on a Beckman L8-80M ultracentrifuge at 26,000 rpm (SW28 rotor) at 20° C. for 1.5 hours. The pellet was resuspended in 1–2mL of phosphate buffered saline (PBS, 2.67 mM KCl, 1.15 mM KH₂PO₄ 137.9 mM NaCl, 8.06 mM Na₂HPO₄ pH 7.4) and then stored at −70° C. until use.

The cell pellet was washed in 30 mL of PBS and spun down again in the GP centrifuge. The pellet was resuspended in 10 mL of PBS then sonicated on ice for 45–50 seconds at 40% power (Cole-Parmer Ultrasonic Homogenizer 4710). The cell lysates were spun down on the GP centrifuge at 900×g for 10 minutes. The pellet fraction I, was resuspended in 1–2 mL of PBS and was held at 4° C. until use. The supernatant was spun down in a Sorvall RC-5 centrifuge with an SS-34 rotor at 10,000 rpm at 4° C. for 30 minutes. The pellet fraction II, was resuspended in 1–2 mL of PBS and held at 4° until use. The supernatant was spun down on the Beckmann ultracentrifuge under the same conditions as the extracelluar protein. The resulting pellet, fraction III, was resuspended in 1–2 mL of PBS and the supernatant was discarded. Fractions II and III were combined to form the intracellular protein stock. The resulting pellet was further purified by sucrose gradient (20%–60%) ultracentrifugation at 26000K rpm (SW28 rotor) for 3 hours at 20° C. The purified insoluble proteins were washed in PBS and then spun down on an IEC Micro-MB centrifuge for 5 minutes at room temperature. The pellet was washed twice more then stored at −70° C. until further use.

EXAMPLE 5

Flow Cytometry—r-FIFA Assay for the Detection of HIV-1 Antibodies

1. Flow Cytometry

Flow cytometric analysis was performed on a Becton Dickinson FACSort equipped with an argon ion laser tuned at 488 nm. Data acquisition was done with Lysus II 2.0 software, version 1.1 (Becton Dickinson). Forward light scattering, orthogonal light scattering and two fluorescent signals were determined on logarithmic settings for each of 20,000 events and stored in data files. Detector settings had been determined and stored in data files for recall by the operator. Data analysis was also performed with the Lysis 2.0 software. A two dimensional dot intensity plot of forward light scatter versus orthogonal light scatter was observed on ungated events. A region (R1) was set on the dot plot and single parameter histograms of FL1 (green emission for FITC is 530 nm) and FL2 (red emission for R-PE is 585 nm) were examined. The median fluorescence channel was used to determine positivity of the test samples. This analysis procedure has also been automated and stored as a command file.

2. r-FIFA Procedure

In 1.5 mL microcentrifuge tubes (Sarstedt) 4 µL of control or sample (plasma or serum) and a pre-determined amount of recombinant protein were combined along with PBS (containing $NaN_3$) to a final volume of 100 µL. Most of the tests were done with a mixture of gag-p45 and gag-gp41-B recombinant proteins. The rest were done with a single antigen as indicated. The tubes were gently vortexed then incubated at ambient temperature for 20 minutes on a rocker. The mixture was washed in 1 mL of PBS/tube and spun down for 5 minutes, ambient temperature at 12 700×g on an IEC Micro-MB centrifuge (fixed speed). The supernatant was aspirated and the pellet was gently resuspended in 1mL PBS and spun down as before. The supernatant was aspirated and 10 µL of FITC and/or R-PE labelled antibody is added. The mixture was incubated for 20 minutes at ambient temperature in the dark then washed two times with 1 ml/tube of PBS as before. After the second aspiration, 500 µL of PBS was added to each sample tube and the mixture was sonicated for 10 seconds at the 40% power setting with a 2 mm diameter probe attachment. The contents were then transferred to 12×75 mm polystyrene tubes (Becton-Dickinson, specific for the flow cytometer) and stored for 2 hours in the dark at ambient temperature then read on the flow cytometer.

To determine the cut-off values of fluorescence intensity for r-FIFA for each of the antigens (gag-p45, gag-gp41-C, pol97, and the mixture of gag-p45 and gag-gp41-B proteins) 100 normal donors were tested by using double staining with IgG FITC and IgM R-PE. Each sample was tested in duplicate and reported in relation to the mean value of a known seronegative control (S/N). The cut-off value was calculated by taking the mean S/N value of the population ($\bar{x}$) and adding two standard deviations (2 SD) as described by Sligh (Sligh, 1989, Amer. J. Clin. Pathol. 91, 210–214). For example, the cut-off value of fluorescence intensity of gag-p45 was calculated as follows:

$$IgG\ FITC\ \bar{x}\ S/N = 0.960$$
$$1\ SD = 0.266$$
$$\text{cut-off} = \bar{x}\ S/N + 2\ SD = 1.48$$

$$IgM\ R\text{-}PE\ \bar{x}\ S/N = 1.666$$
$$1\ SD = 0.581$$
$$\text{cut-off} = \bar{x}\ S/N + 2\ SD = 2.83$$

$$IgA\ R\text{-}PE\ \bar{x}\ S/N = 1.270$$
$$1\ SD = 0.604$$
$$\text{cut-off} = \bar{x}\ S/N + 2\ SD = 2.48$$

Sample to cut-off (s/c) ratios of 1.0 or greater are considered positive.

EXAMPLE 6

Sensitivity and Reproducibility of r-FIFA

Figure 8A:
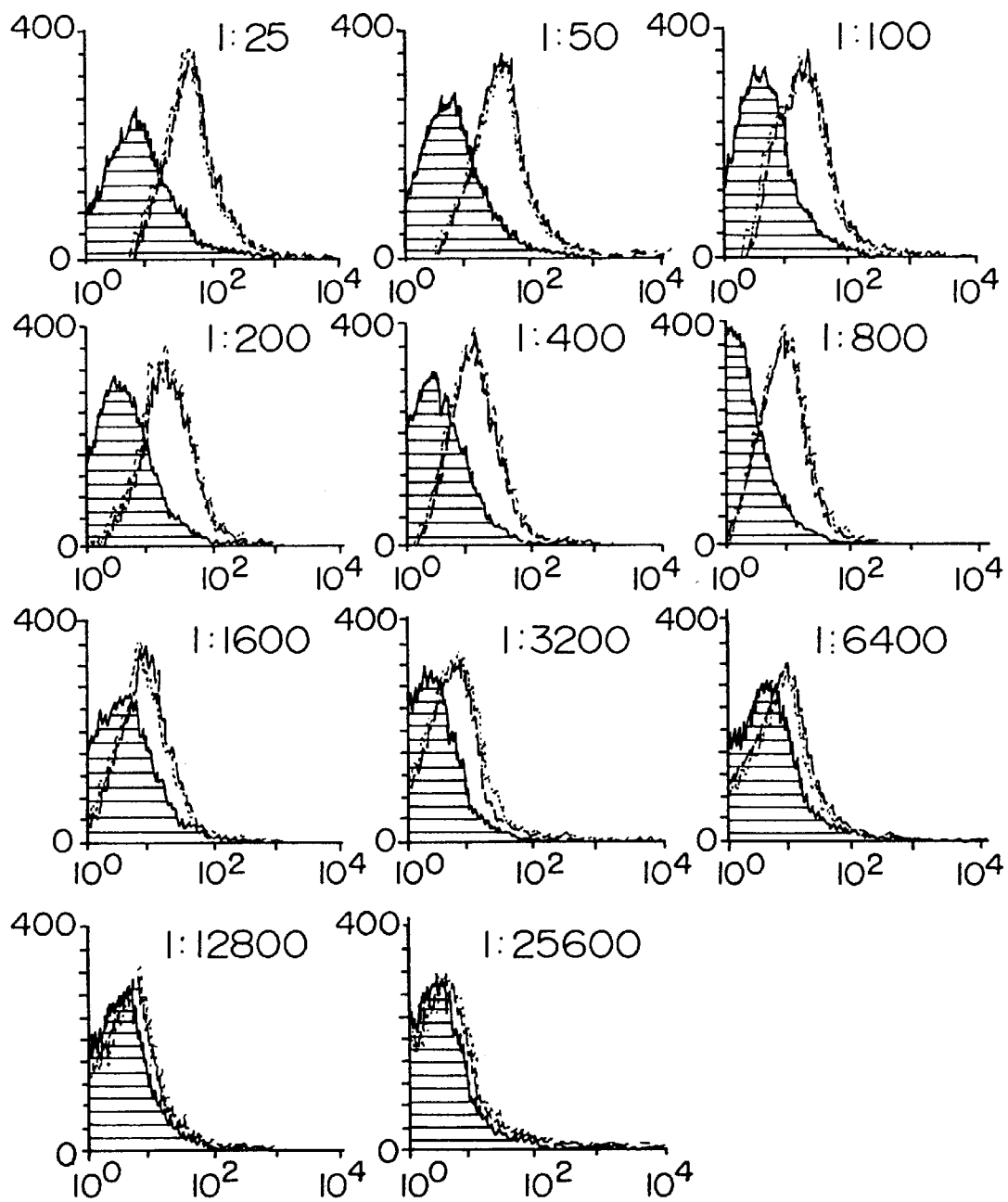
FIGS. 8A–8D represent the titration of HIV-1 seropositive plasma using gag-p45 as the antigen in r-FIFA.
Figure 8B:
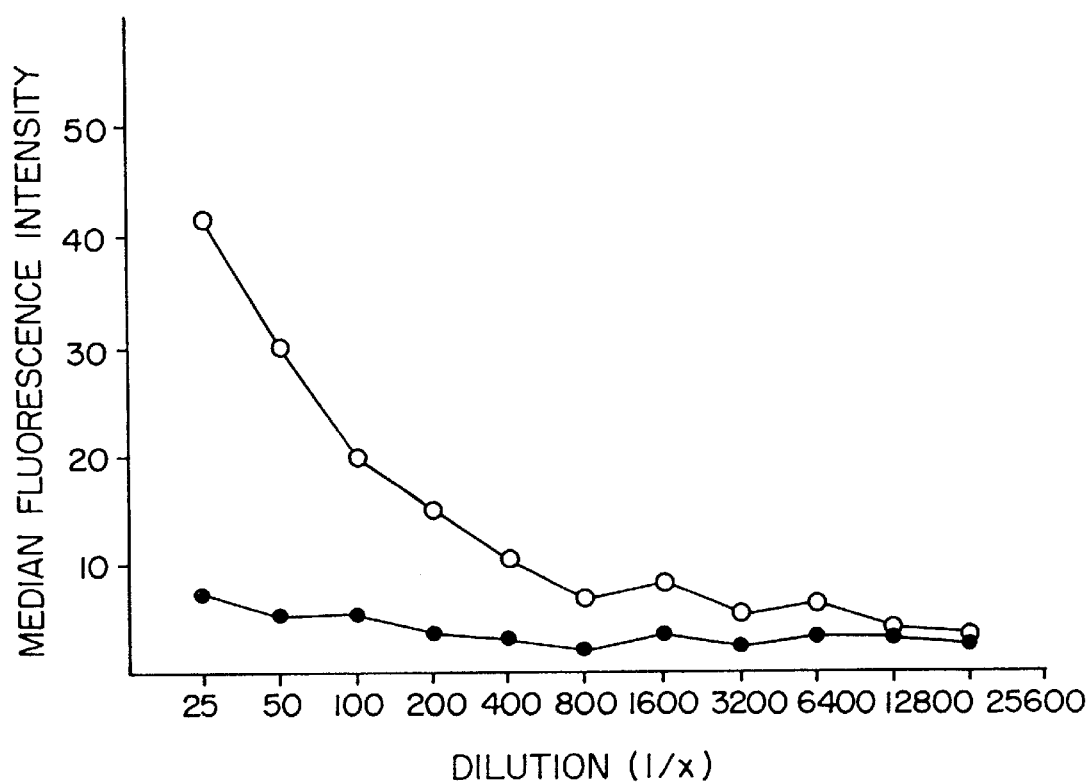
Figures 8C, 8D:
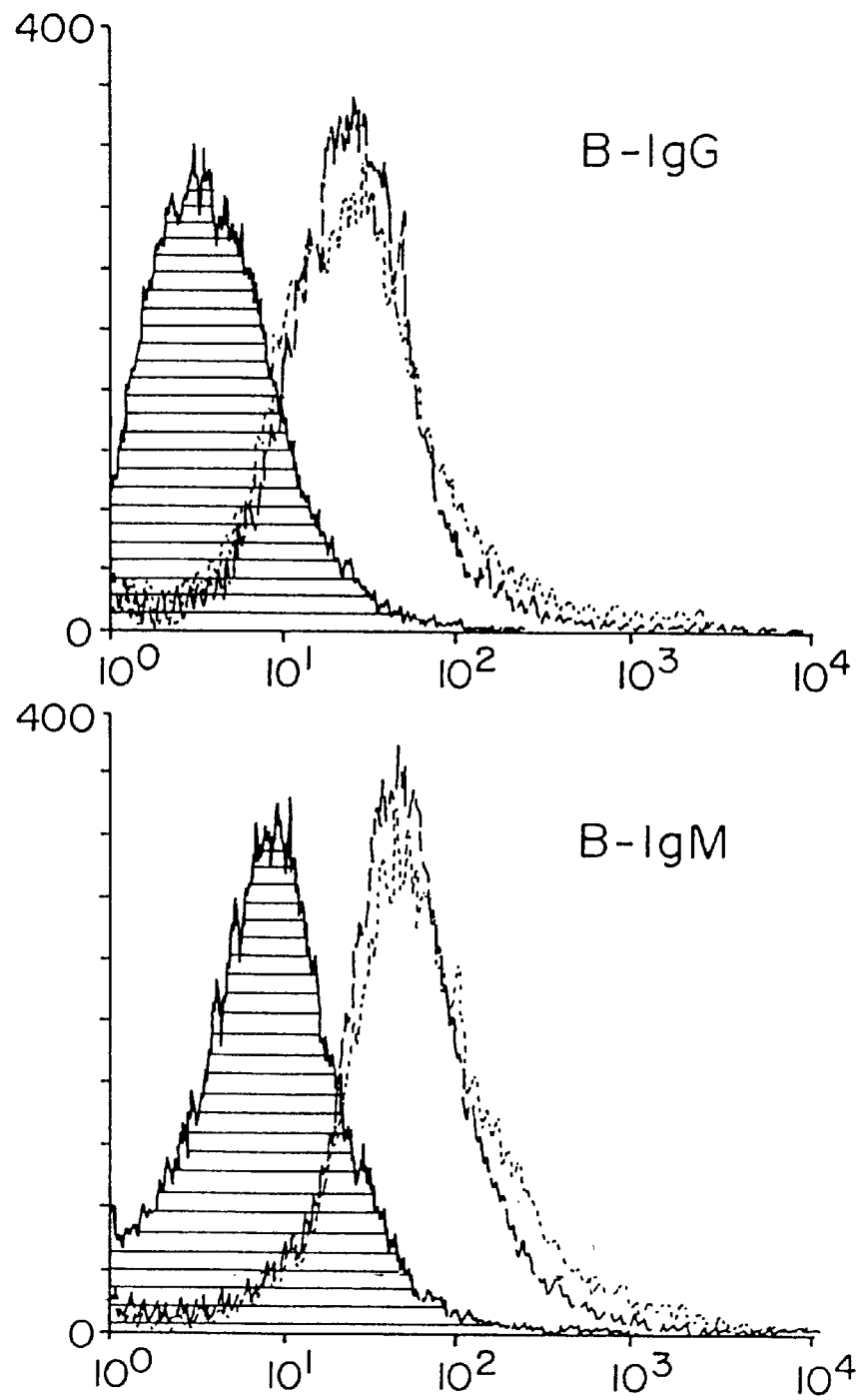

In order to determine the optimal serum or plasma dilution required for the sensitivity test of r-FIFA, an HIV-1 seropositive plasma and a control (negative plasma) were treated with gag-p45 as the antigen. FIG. 8 shows the fluorescence histograms of the samples at different dilutions. The fluorescence intensity of the positive sample sharply decreased as the dilution increased. It was positive at 1:6400 (s/c=1.25). The 1:25 dilution was shown to be the optimal sample dilution for r-FIFA and this dilution was used for further experiments.

Figure 9:
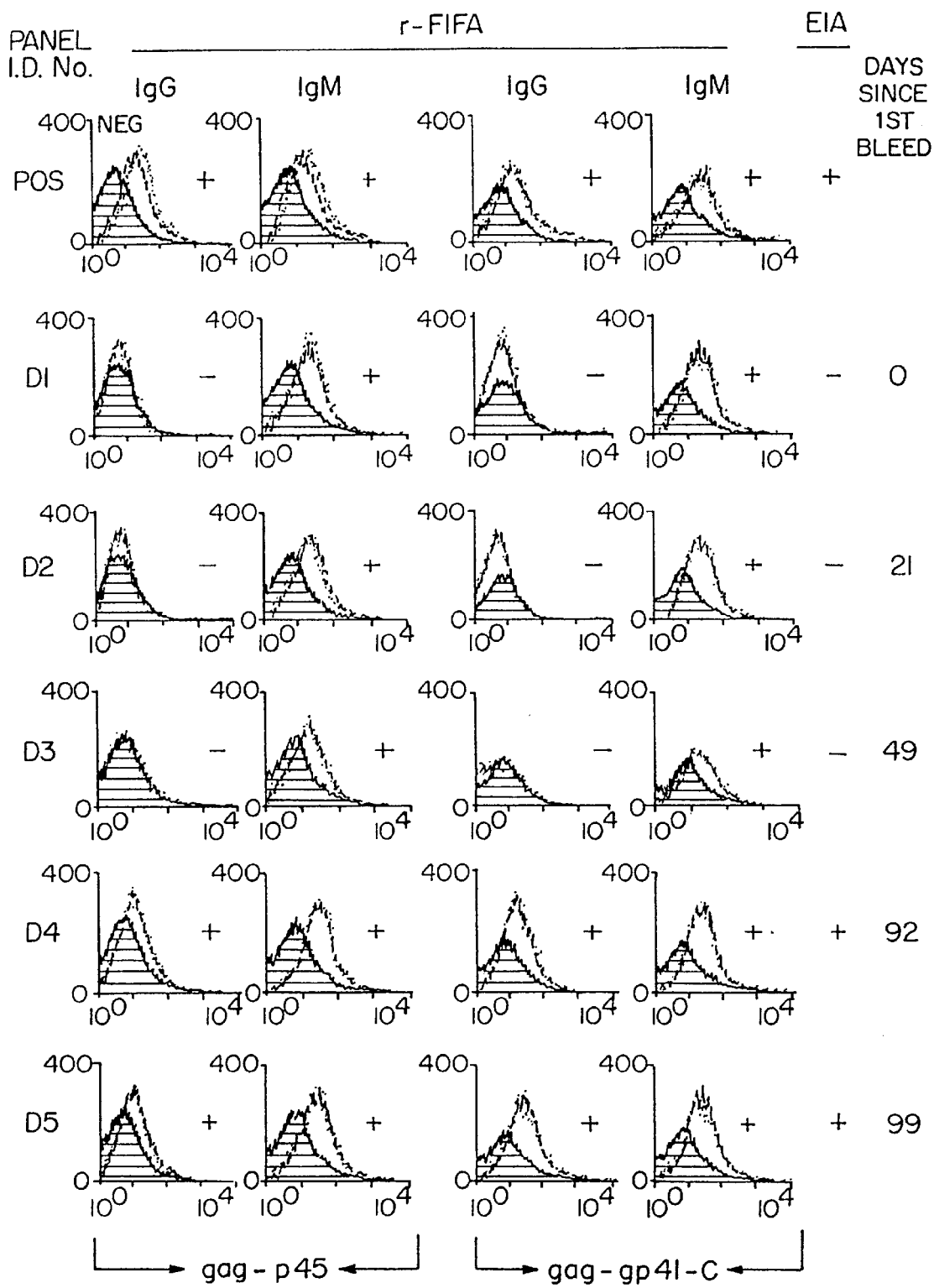
FIG. 9 represents early HIV-1 antibodies detection in the samples of BB1 anti-HIV-1 seroconversion panel D by r-FIFA using two different antigens. The flow cytometric histograms show anti-HIV-1 antibody signals in those samples (line peaks) and fluorescence signal (background) of the negative sample as control (solid grey peak)

Table 1 summarizes the results of r-FIFA for detection and analysis of eight BBI anti-HIV-1 seroconversion panels and compares the sensitivity of r-FIFA with currently licensed tests. Anti-HIV-1 antibodies were detected by r-FIFA in the first bleed of seven BBI panels. The average increase in sensitivity was greater than 20 days. FIG. 9 illustrates the fluorescence histograms of samples in Panel D. The HIV-1 antibody (IgM) had become positive three months before antibodies were detected by EIA. The antibody titer dropped in sample D3 possibly because of HIV antigen-antibody complex formation.

Figure 10A:
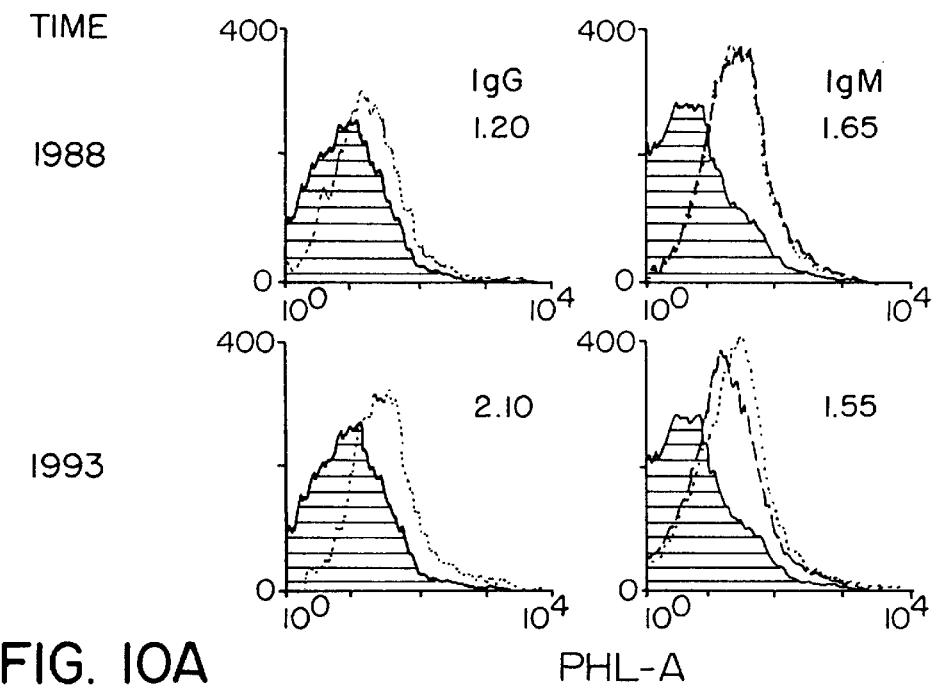
Figure 10B:
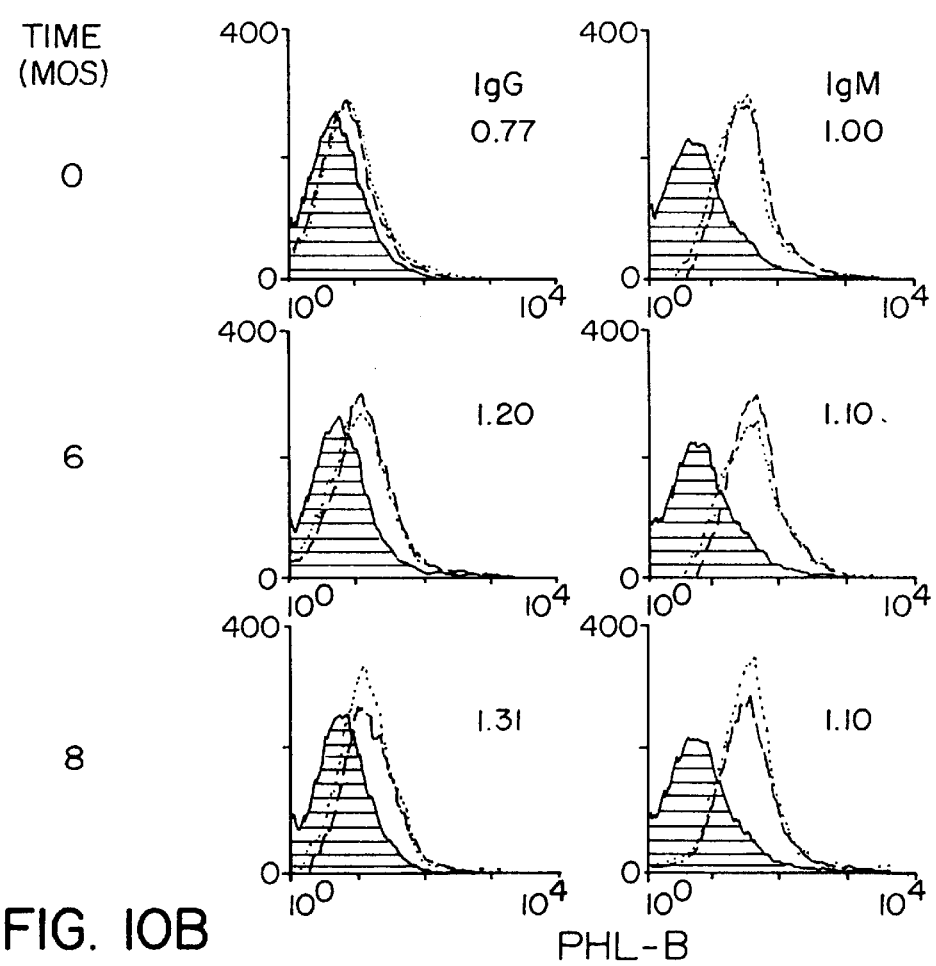
Figure 11A:
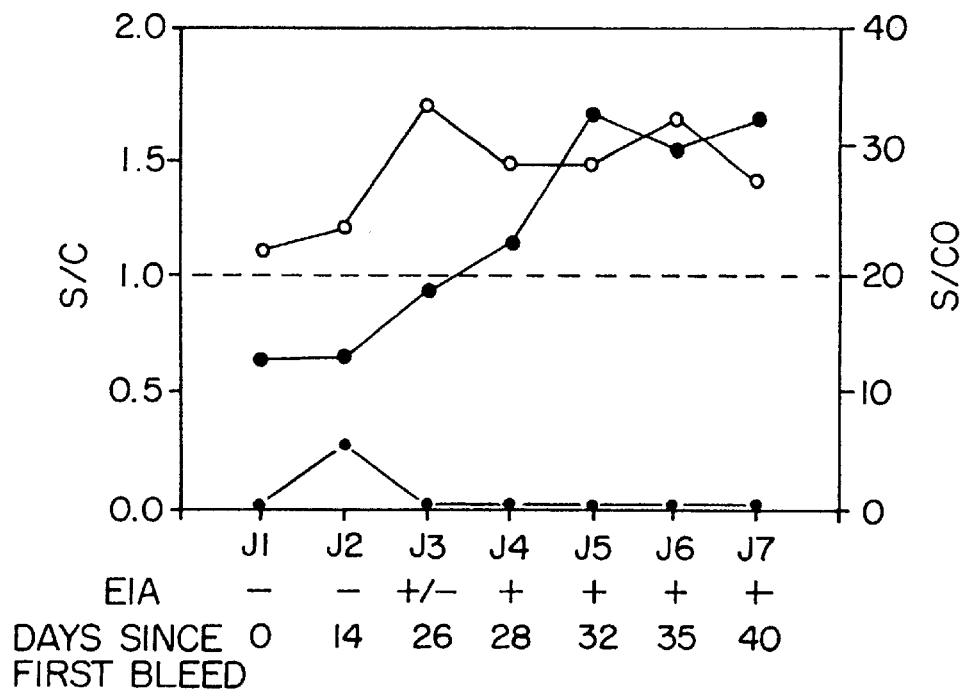
FIGS. 11A–11H represent antibody response during the window period of HIV-1 infection. In this kinetic analysis of IgM and IgG antibody production the results are expressed by median fluorescence intensity ratio of sample to cut-off (s/c) value (left axis). The broken line represents the antibody s/c value level of 1.0. The s/c value on this line or higher is considered positive. The right axis represents the s/c (s/co) value of HIV-1 antigens. A typical primary immune response was found in panels (FIG. 11A), K (FIG. 11C), D (FIG. 11E) and R (A) (FIG. 11G). The immune response pattern in panels E (FIG. 11B), H (FIG. 11D), P (FIG. 11F) and Q (B) (FIG. 11H) is different from the pattern seen in (FIGS. 11A, 11C, 11E and 11G). IgG is the dominant antibody and remains at low level for a long period. (○) represents IgM antibody to HIV-1, (●) represents IgG antibody to HIV-1 and (▼) represents HIV-1 antigen.
Figure 11B:
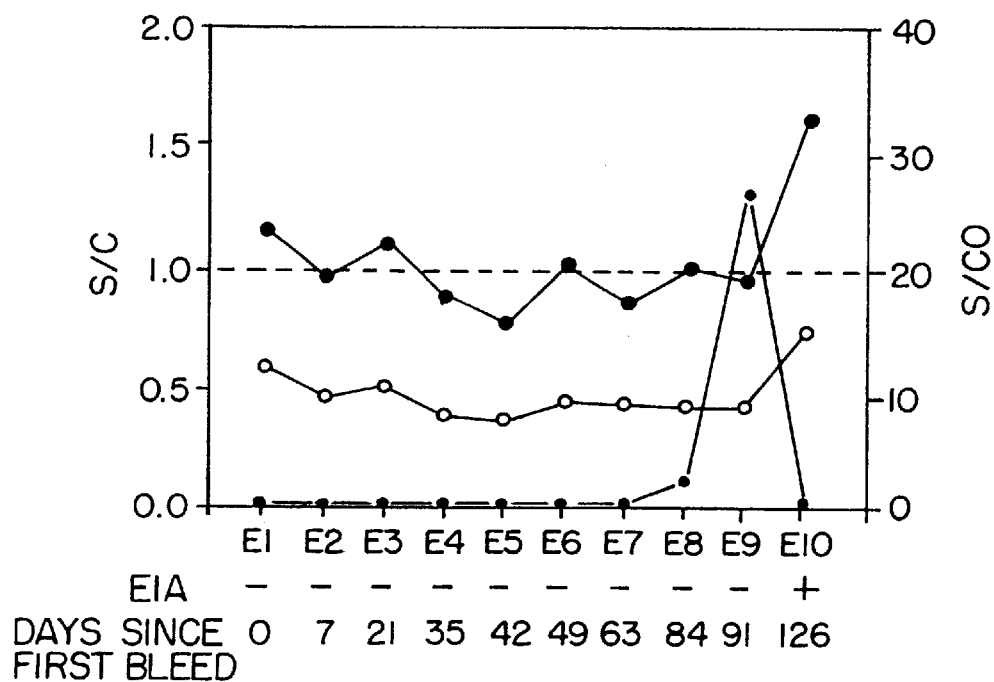
Figure 11C:
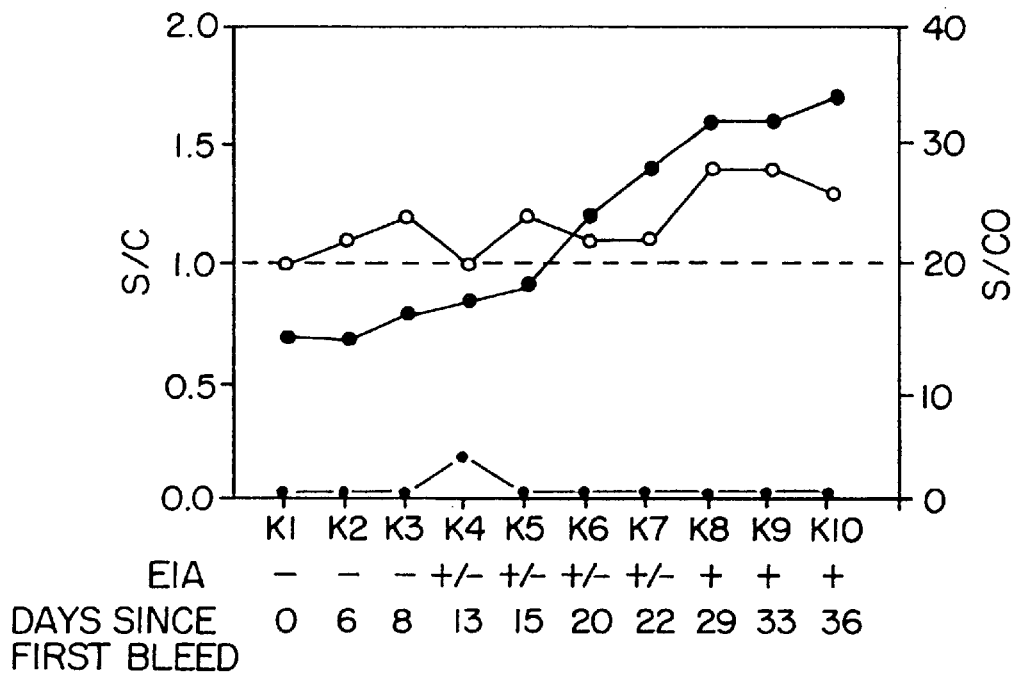
Figure 11D:
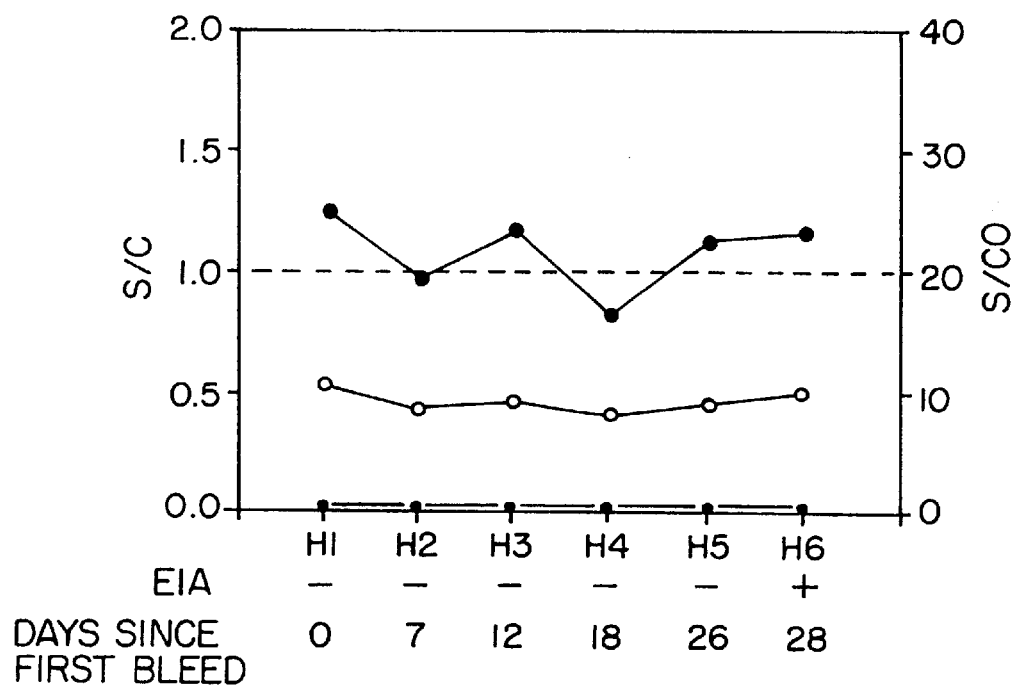
Figure 11E:
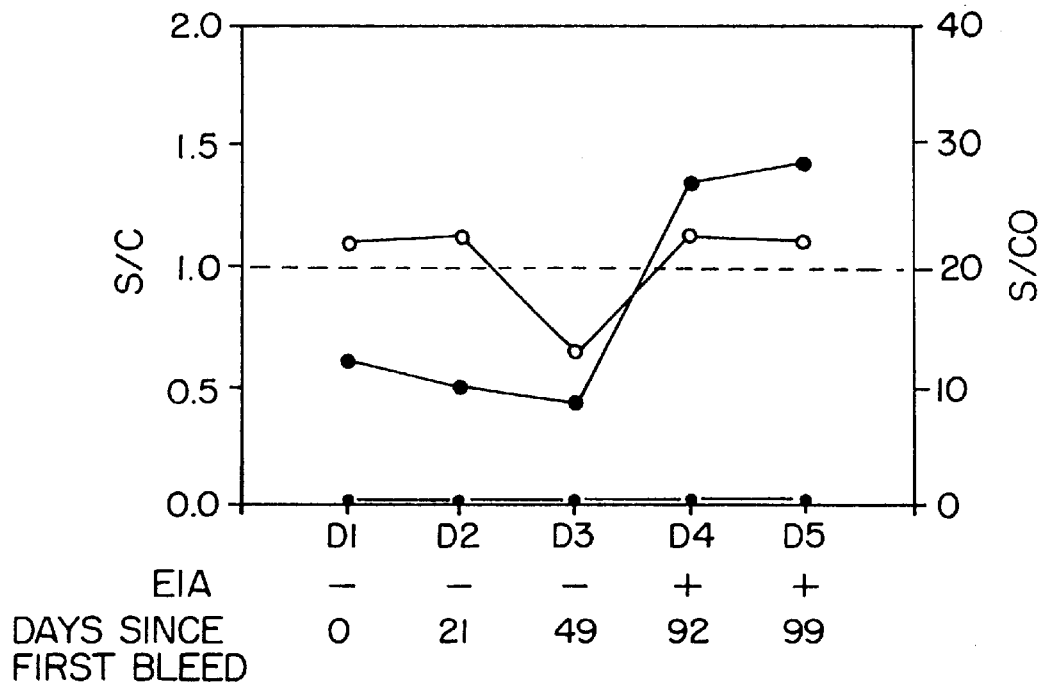
Figure 11F:
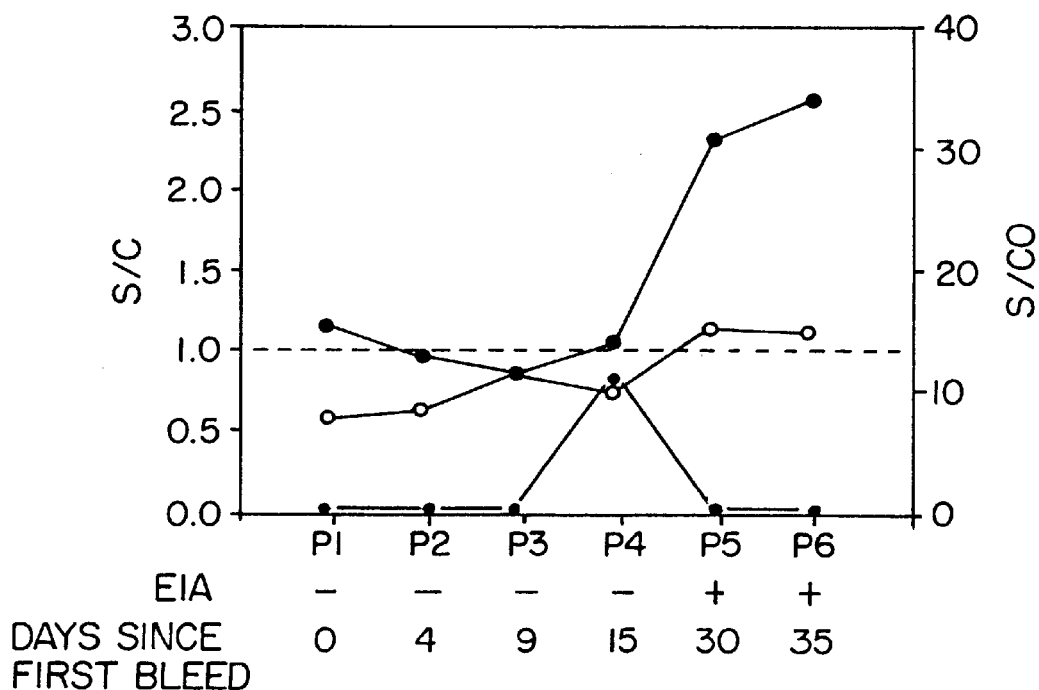
Figure 11G:
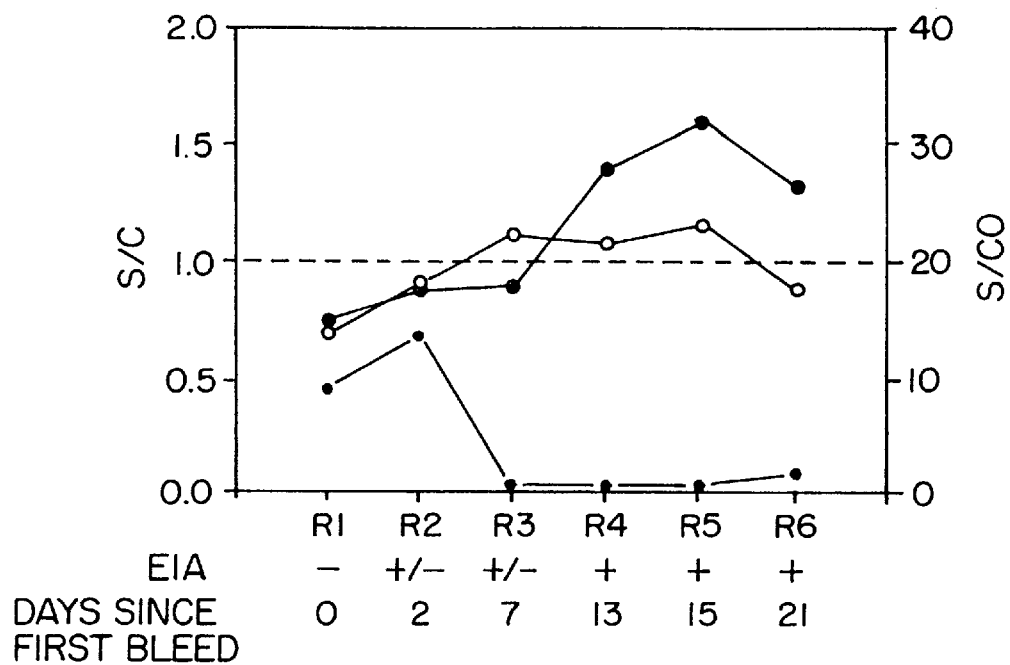
Figure 11H:
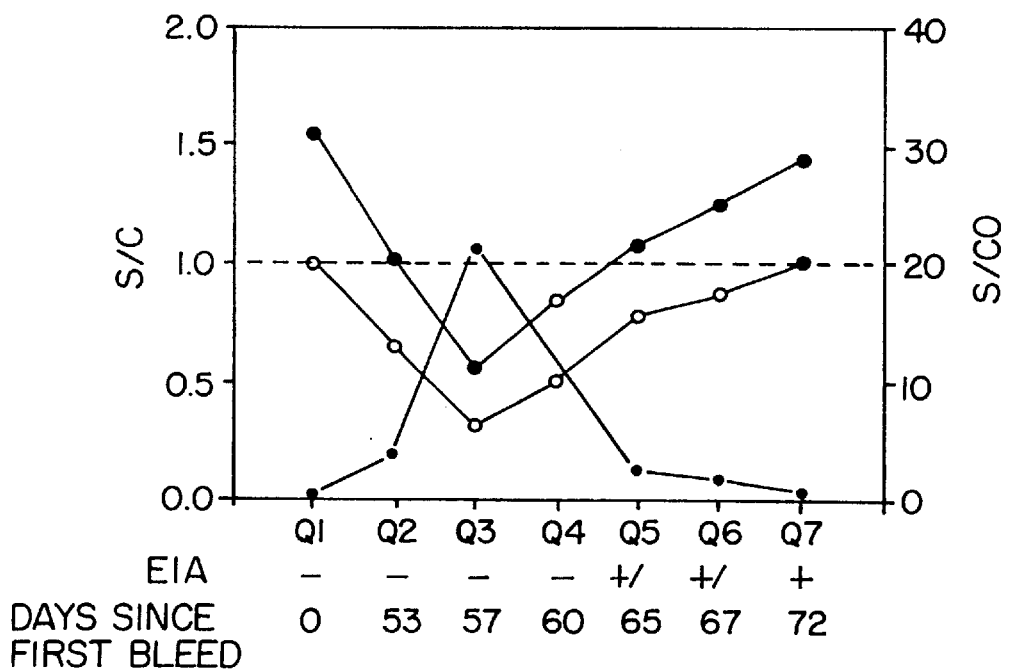
Figure 15:
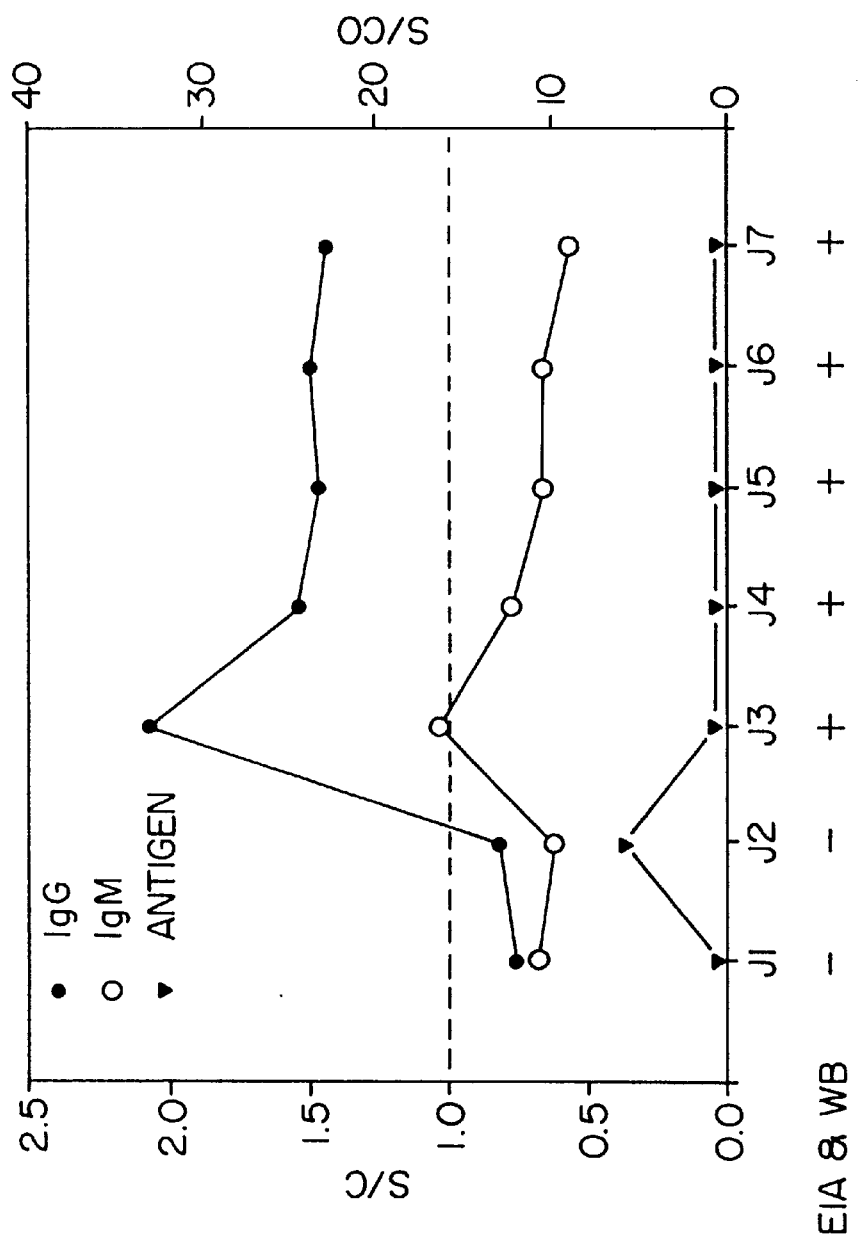
FIG. 15 represents antibody response to HIV-1 RT precursor pol97 polyprotein tested by r-FIFA during early HIV-1 infection in the anti-HIV-1 seroconversion performance panel J(BB1). The axises represent the s/co value of HIV-1 antigens (right) and the sample to cut-off ratio (s/c) of antibody to pol97 (left). The broken line represents the antibody s/c value of 1.0.

To evaluate the reproducibility of r-FIFA, two antigens gag-p45 and gag-gp41-C were used for the analysis of panel D. The results of the two assays were almost identical. The duplicates of each assay were highly reproducible as shown by the overlapping of two line peaks which represent the fluorescent intensity of each sample. In addition to the BBI panels, three HIV-1 seroconversion panels from PHL were evaluated in a blind test to confirm the sensitivity of r-FIFA (FIG. 10). The first bleed of all three patients was seronegative in EIA and WB tests. However, IgG and IgM HIV-1 antibodies were detected by r-FIFA. The antibody response pattern of the three panels suggests that the patients were infected recently since IgM was the dominant antibody. The first bleed from the patient PHL-A (who donated blood for a transfusion) was negative by EIA in 1988. The recipient was infected by the seronegative but HIV-1 infected blood. The donor was identified as HIV-1 positive by testing in 1993 with a recently licensed test which used conjugated second antibody to both human IgG and IgM. The 1988 sample was still negative by this test but the 1993 sample was strongly positive. In r-FIFA, both the 1988 and the 1993 samples were positive for IgG and IgM. Furthermore, to compare the sensitivity of r-FIFA with that of FDA licensed confirmatory tests including WB, and radioimmunoprecipitation (RIPA), the BBI anti-HIV-1 1 ow titer panel was tested with r-FIFA using each of the antigens gag-p45, gag-gp41 chimeric proteins and pol97. The results are summarized in Table 2 and show that r-FIFA is more sensitive than any of the FDA licensed confirmatory tests. The antibodies to gag and env or to all three of these antigens were positive by r-FIFA in 12 of the 14 samples. Only 8 to 10 were positive in the four confirmatory tests. The results show that the pol97 is an excellent antigen for HIV-1 antibody detection. Antibodies to pol97 were detectable in 8 out of the 14 samples in r-FIFA. However, the antibodies to pol gene products (p68, p51 and p31) were poorly detected in the FDA licensed confirmatory tests. Only 1 to 4 of the 14 samples were found to have antibodies to pol proteins on WB and RIPA. It has been reported that antibodies to gag-encoded proteins appear first, followed closely by those antibodies to env glycoproteins, then pol reactivity to p66 appear on WB. Our studies show that the antibodies to pol97 were detected as early as those to gag-p45 and gag-gp41 chimeric proteins as shown in FIG. 15. This provides evidence to the effect that antibodies to pol gene products are one of the important serological markers for early diagnosis of HIV-1 infection and monitoring of HIV-1 infection disease progression.

EXAMPLE 7

Specificity of r-FIFA 295 random donor samples, 105 EIA/WB positive samples and 128 EIA repeat reactive or positive/WB indeterminate samples were tested by r-FIFA. Only 1 of the 295 random donor samples was positive. One of the positive samples from the random donor was negative in EIA but was positive by radioimmunoprecipitation (r-RIPA). All 105 positive samples were positive by r-FIFA. Only 30 of 128 (23%) EIA repeat reactive WB indeterminate samples were still positive. These results indicate that r-FIFA's specificity is higher than that of EIA and WB.

EXAMPLE 8

Antibody Response During the Window Period

Figure 12:
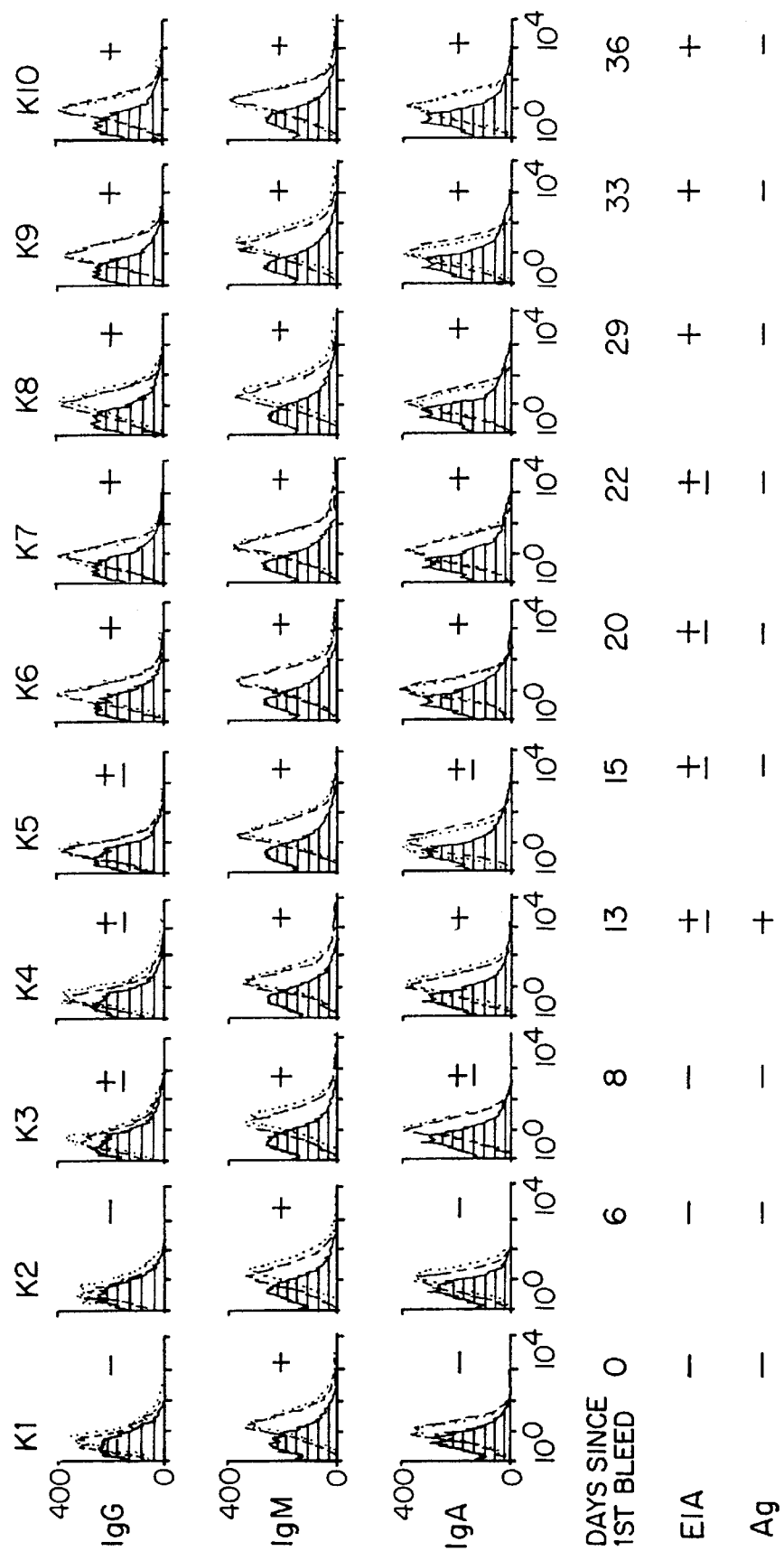
FIG. 12 represents the kinetics of the immune response during the window period of HIV-1 infection. The fluorescence histograms of samples in BB1 panel K represent IgG, IgM and IgA antibody production showing the phases of primary response at a very early stage of HIV-1 infection. IgA antibody in samples K1 and K2 are significantly stronger than the negative control, but they are still negative by our criteria because the s/c value is higher for IgA than for IgG.

FIG. 11 demonstrates the patterns of HIV-1 antibody production in eight BBI panels. A typical primary response was found in panels J and K. Panels D and R show a similar pattern of antibody production. However, in panels E, H, P and Q, the HIV-1 IgG antibody remained at a certain level for a long period (over two or three months) prior to seroconversion as detected by licensed tests. The IgM antibody became positive later at a low level or at the same time (panel Q) as did IgG antibodies. The pattern of E, H, P and Q is apparently different from the pattern of D, J, K and R. Presumably these individuals were not recently infected by HIV-1. For some reason, virus-antigen concentration rose, stimulating the antibody response. The anti-HIV-1 IgG antibodies jumped up to a high level in a shorter time (less than a week as seen in Q and R) indicating a possible secondary immune response. FIG. 12 shows the fluorescence histograms of the samples in panel K, indicating the kinetics of the specific IgG, IgM and IgA production during the window period. The IgM antibodies were detected first before the antigen was detected, and then IgA and IgG antibodies appeared about two weeks after the antigen level peaked. The IgM antibody response to HIV-1 proteins overlapped with the HIV-1 antigen peak and started before the antigen was detected.

EXAMPLE 9

Figures 13A, 13B:
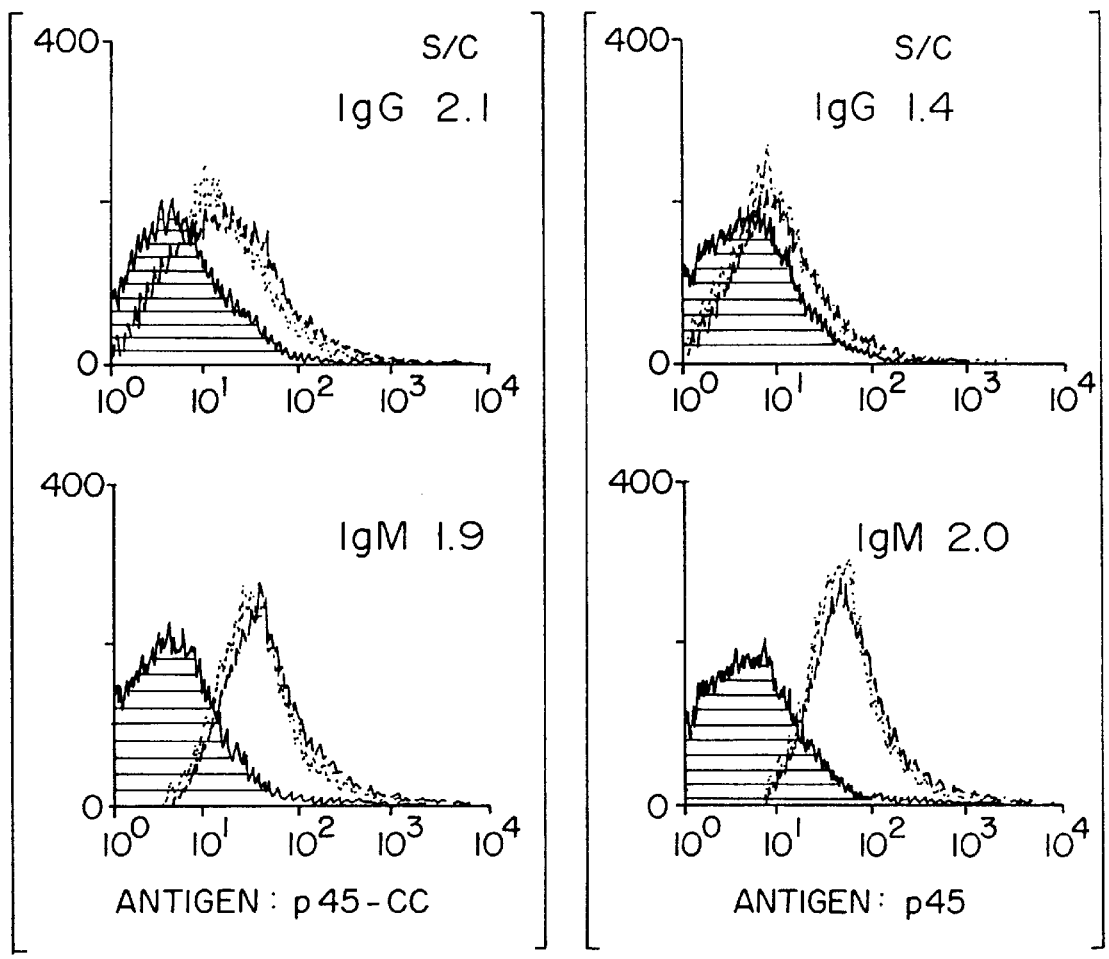
FIGS. 13A and 13B represent antibody detection using antigen gag-gp41-C (p45-cc, FIG. 13A) and gag-p45 (p45, FIG. 13B) in r-FIFA.
Figure 13C:
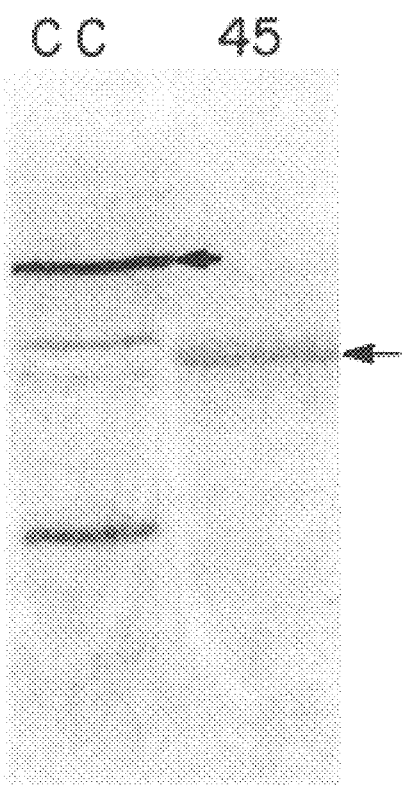
Figure 13D:
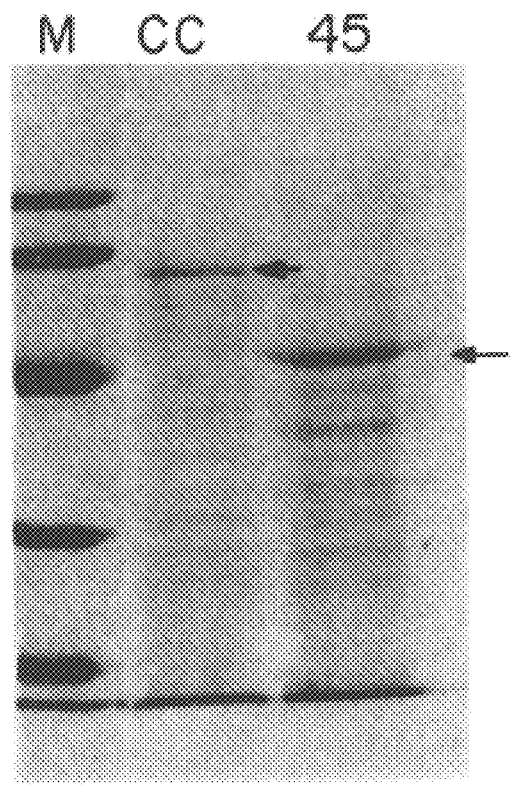
Figure 14A:
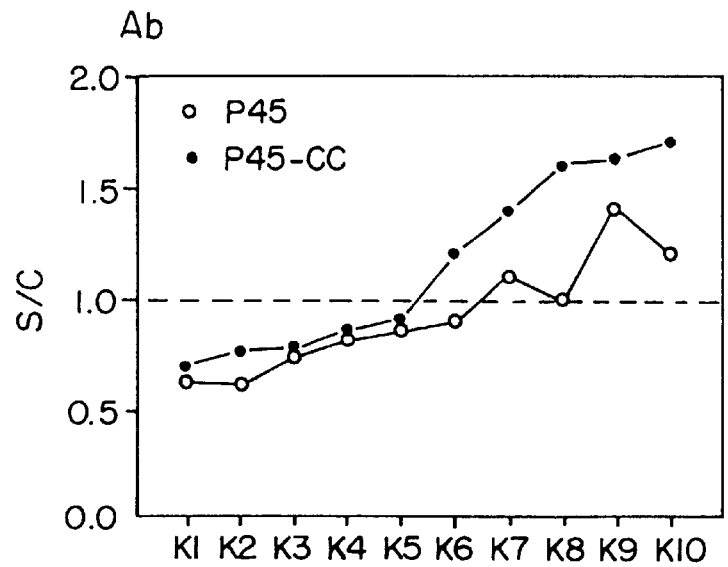
FIGS. 14A–14C represent HIV-1 early antibody (IgG) detection by using the gag-p45 antigen and the antigen chimeric gag-gp41-C (p45-cc) in r-FIFA. The results shown indicate that chimeric antigen gag-gp41-C (p45-cc) detects the antibodies earlier and with a stronger signal than the antigen gag-p45 does during the early stage of HIV-1 infection
Figure 14B:
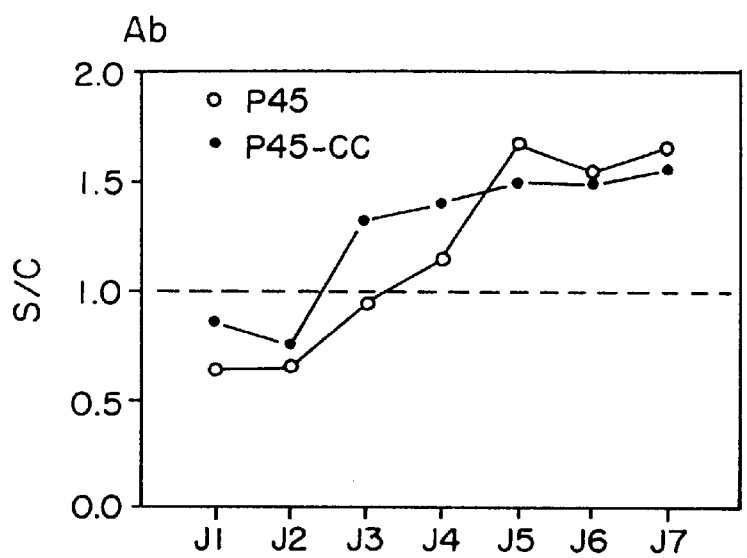
Figure 14C:
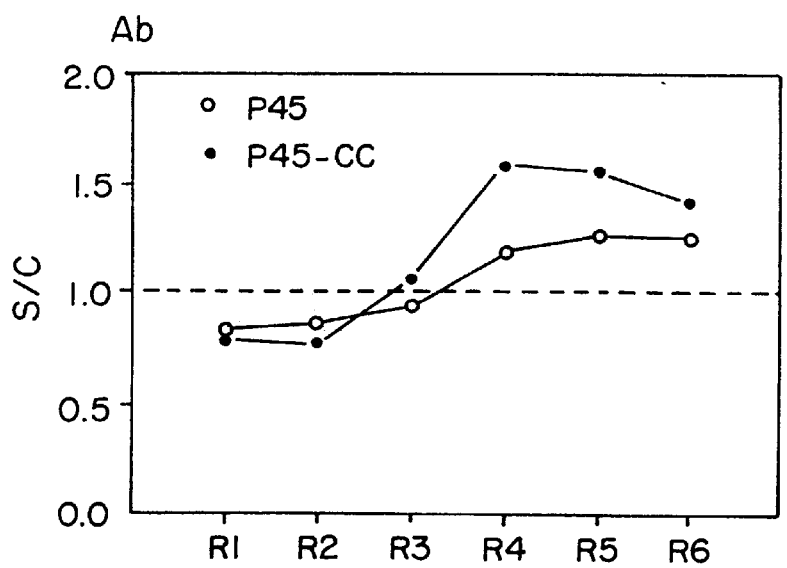

Differences in Antibody Response to Different Antigens gag-p45, gag-gp41-C and pol97 in r-FIFA Chimeric gag-gp41-C binds more IgG antibodies than gag-p45 and detects them earlier. Little difference was found in detection of HIV-1 IgM antibodies (FIGS. 13 and 14). HIV-1 IgG antibodies to pol97 were detected as early as gag-gp41-C (FIG. 15). IgM antibody to pol97 was very low during this "window" period.

EXAMPLE 10

Comparison of r-FIFA Assay with gag-p45, gag-gp 41-C, pol97, gp 160 and Mixture of gag-45, pol97 and gp 160

In a preferred embodiment, a mixture of equal amounts of gag-p45, pol97 and gp 160 is used in the r-FIFA. The proteins were prepared as described in the previous examples and the r-FIFA was conducted as previously described. An anti-HIV-1 low titer performance panel (PRB 104) was utilized. The results are reported in Table 3. The testing with a mixture of all three proteins was carried out with 5 samples. The results with the mixture were positive in all instances. This shows the sensitivity of the procedure with a mixture of the proteins. In instances where the results were negative for each of the four proteins individually, the results with the mixture were negative as well (sample 10) and where the results were positive with each of the proteins individually, the results of the mixture were positive as well (sample 7). The use of a mixture of the proteins is advantageous in a situation where the results with each of the proteins all not all positive or negative (samples 3, 11 and 14). In all instances where some of the individual results were negative, the use of a mixture of proteins allowed a final determination and gave positive results. The gag, gp and pol polyproteins cover over 90% of the viral structural proteins and allow r-FIFA to be used as a confirmatory test because of its high sensitivity, specificity and its ability to identify antibodies directed to individual HIV-1 polyproteins.

EXAMPLE 11

Flow Cytometry—r-FIFA Assay for the Detection of Hepatitis B Antibodies

The Hepatitis B core antigen was prepared as is known in the art and as is described for example in Takehara et al., 1988, J. Gen. Virology, 69:2763–2777. Recombinant baculoviruses were constructed to express the hepatitis B core antigen in the same manner as described in Example 1 in relation to HIV-1 gag p45 and chimeric gag-gp 41 proteins. The r-FIFA assay for the detection of antibodies to Hepatitis B core antigens was conducted as set out in Example 5 in relation to the detection of HIV-1 antibodies. The results of a comparison of sensitivity between licensed EIA and RIA tests for Hepatitis B and r-FIFA using standard BBI panels are set out in Table 4.

The above examples demonstrate that r-FIFA is more sensitive than licensed screening and confirmatory tests for detection of early antibodies to HIV-1. At least one class of anti-HIV-1 specific IgG, IgM or IgA was detected during the window period of HIV-1 infected individuals. We have created a unique way to detect early antibodies using insoluble forms of recombinant proteins as autologous carriers through a flow cytometer. Two patterns of antibody response were observed, which may represent two types of immune response: primary and secondary.

Figure 16:
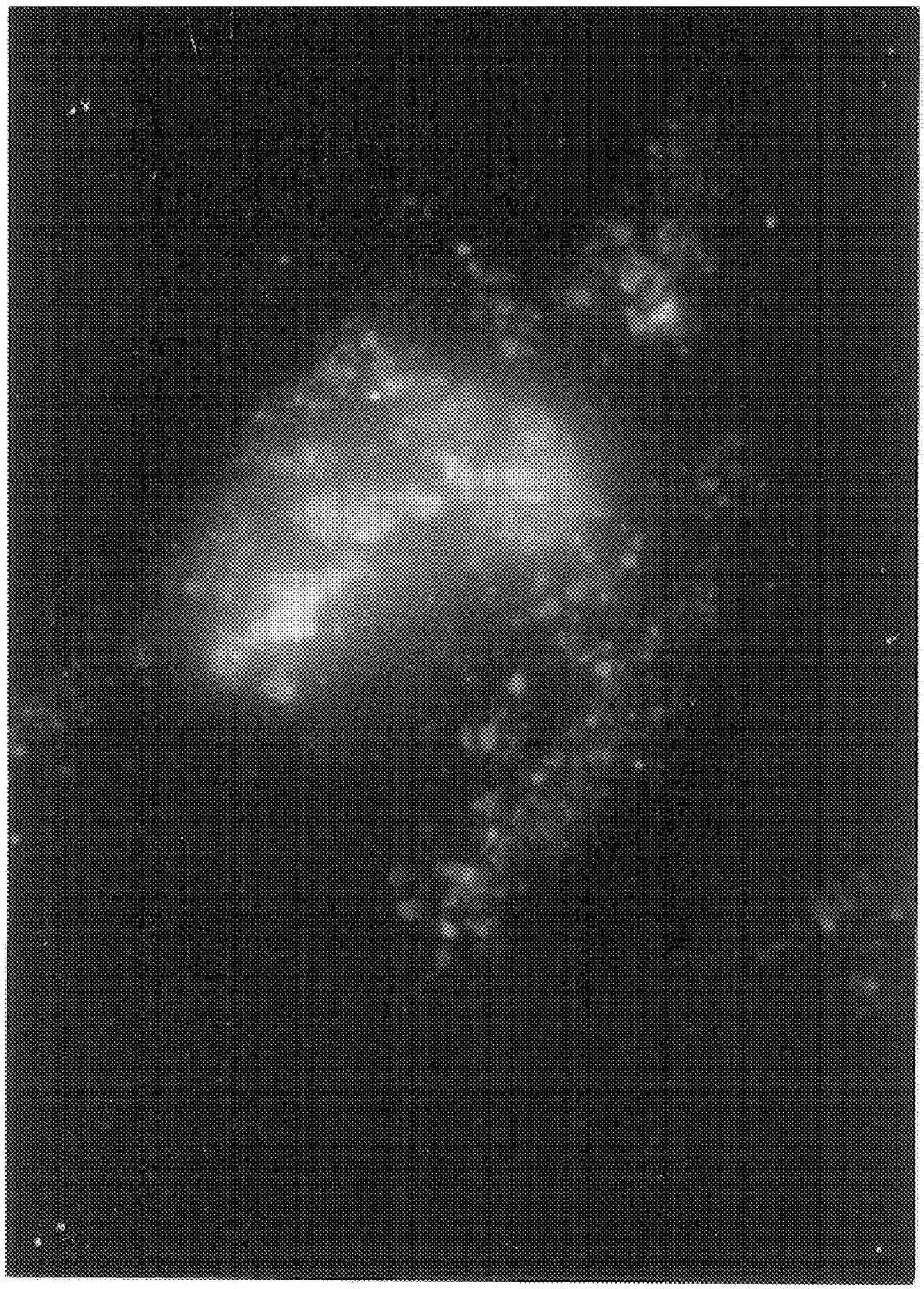
FIG. 16 represents the detection of antibodies to HIV-1 gag-p45 particles by indirect immunofluorescence. The HIV-1 antibody bound gag-p45 particles were stained with goat antihuman IgG FITC and IgM RPE conjugates showing the HIV-1 specific antibodies IgG (green fluorescence) and IgM (orange yellow fluorescence).

On average for the tests which were in use in 1990 the window period was 45 days. Since then the tests have increased sensitivity for HIV antibody detection resulting in earlier detection of seroconversion and a significant decrease of approximately 12–13 days in the length of the infectious window period (Dodd, 1990, Arch. Pathol. Lab. Med. 114, 240–245). An analysis of the records made in 19 American National Red Cross regions in 1992 and 1993 showed that the window period estimated using third generation tests was 25 days on average Petersen et al., 1994, Transfusion 34,283–289). As shown in Table 1, the average increase in sensitivity using the method of the present invention was greater than 20 days. The r-FIFA of the present invention is a novel serological test, which uses insoluble polyproteins. The insoluble antigens are easily processed and purified without denaturation, keeping intact their natural molecular folding which may optimize the presentation of antigen epitopes. This may be one of the explanations to account for r-FIFA's higher sensitivity in detection of HIV-1 early antibodies. Furthermore, an agglutination effect involving the reaction between IgM antibodies and the antigens in r-FIFA may enhance the sensitivity for detection of specific antibodies because all the insoluble polyproteins used are particulate antigens. This is demonstrated in FIG. 16. In general, IgM antibodies are more efficient in agglutination than IgG antibodies because of their size as well as their additional binding sites.

The assay of the present invention (r-FIFA) is much more sensitive than any of the currently licensed tests used for analysis of BBI seroconversion panels to detect very early HIV-1 antibodies during the "window" period. Both anti-HIV-1 specific IgG and IgM have been found prior to the seroconversion of seroconversion panels. Some of them contain primarily anti-HIV-1 IgG or IgM. Some individuals have both anti-HIV-1 IgG and IgM. This appears to depend on the time of primary infection, appearance of antigenemia and the situation of the immune system of the HIV-1 infected individuals. Detection, quantification and differentiation of anti-HIV-1 antibodies in the "window" period have permitted a further understanding of the immune response and HIV-1 immunopathogenesis in this "immunological silent" period. The development of r-FIFA has allowed the use of insoluble proteins as antigens to detect antibodies. These insoluble proteins can be easily produced on a large scale using a baculovirus expression system.

While the r-FIFA procedure for use in the detection of HIV-1 infection is described in relation to gag p45, gag-gp 41, gp 160 and pol97 recombinant proteins, it will be understood that a mixture of these proteins as exemplified in Example 10 can be used as well as any number of other proteins and need not be recombinant proteins prepared in the baculovirus expression system. The proteins are not limited to those specifically exemplified. While the examples and the results set out above pertain to the use of the recombinant proteins in the detection and treatment of HIV-1, it is understood that the examples are not meant to be limiting. The invention would have applicability to the detection and treatment of HIV-2 using an insoluble form of a protein equivalent to gag p45 in HIV-1 as well as have applicability in the detection and treatment of other viral infections. This is illustrated in Example 11 where r-FIFA is used in the detection of hepatitis B. The invention also has applicability in the detection of other viral infections such as hepatitis C, HTLV-1/2 (human T-cell leukemia) or HTLV-II and has applicability for any virus-mediated condition where the virus proteins exist in insoluble form. Indeed, it is not limited to the detection of viral infections but has application for the detection of any disease state where an insoluble form of an antigen can be used in the assay of the present invention for the detection of antibodies. It is also contemplated that chimeric proteins can be constructed comprising several antigenic domains so that one test could be used for the detection of several disease states, for example, HIV-1/2, HTLV-1/2, hepatitis B and hepatitis C.

Furthermore, it is also understood that where recombinant proteins are used in the assay of the present invention, any expression system sharing the advantages of the baculovirus expression system could also be used.

All publications referred to in the disclosure are hereby incorporated by reference.

While the present invention has been described in connection with a specific embodiment thereof and in a specific use, various modifications will occur to those skilled in the art without departing from the spirit and scope of the invention as set forth in the appended claims. I therefore wish to embody within the scope of the patent which may be granted hereon all such embodiments as reasonably and properly come within the scope of my contribution to the art.

TABLE 1

Comparison of the Sensitivity Between r-FIFA and Licensed Tests for HIV-1 Antibodies in Anti-HIV-1 Seroconversion Panels (BBI)

| Code | # of Members | Time Span (Days) | Members Antigen + | \multicolumn{10}{c}{Antibody Reactivity of Each Panel Member} | Tests |
|------|--------------|------------------|-------------------|---|---|---|---|---|---|---|---|---|----|-------|
|      |              |                  |                   | 1 | 2 | 3 | 4 | 5 | 6 | 7 | 8 | 9 | 10 |       |
| D    | 5            | 101              | 0                 | − | − | −   | + | + |   |     |   |   |    | EIA   |
|      |              |                  |                   | + | + | (+) | + | + |   |     |   |   |    | r-FIFA |
| E    | 10           | 126              | 2                 | − | − | −   | − | − | − | −   | − | − | +  | EIA   |
|      |              |                  |                   | + | + | +   | (+) | − | + | (+) | + | + | +  | r-FIFA |
| H    | 6            | 28               | 0                 | − | − | −   | − | − | + |     |   |   |    | EIA   |
|      |              |                  |                   | + | + | +   | + | (+) | + |     |   |   |    | r-FIFA |
| J    | 7            | 40               | 0                 | − | − | +   | + | + | + | +   |   |   |    | EIA   |
|      |              |                  |                   | + | + | +   | + | + | + | +   |   |   |    | r-FIFA |
| K    | 10           | 36               | 0                 | − | − | −   | (+) | (+) | (+) | (+) | + | + | +  | EIA   |
|      |              |                  |                   | + | + | +   | + | + | + | +   | + | + | +  | r-FIFA |

TABLE 1-continued

Comparison of the Sensitivity Between r-FIFA and Licensed Tests for
HIV-1 Antibodies in Anti-HIV-1 Seroconversion Panels (BBI)

| Code | # of Members | Time Span (Days) | Members Antigen + | 1 | 2 | 3 | 4 | 5 | 6 | 7 | 8 | 9 | 10 | Tests |
|---|---|---|---|---|---|---|---|---|---|---|---|---|---|---|
| P | 6 | 35 | 1 | − | − | − | − | + | + | | | | | EIA |
|   |   |    |   | + | + | (+) | + | + | + | | | | | r-FIFA |
| Q | 7 | 72 | 5 | − | − | − | (+) | (+) | + | | | | | EIA |
|   |   |    |   | + | + | − | (+) | + | + | + | | | | r-FIFA |
| R | 6 | 21 | 2 | − | (+) | (+) | + | + | + | | | | | EIA |
|   |   |    |   | − | (+) | + | + | + | + | | | | | r-FIFA |

EIA data shown in this table is a summary of 13 licensed test results from BBI. Both anti-HIV-specific IgG and IgM were detected by r-FIFA using fluorescence conjugated second antibodies to human IgG and IgM. The anti-HIV-1 antibodies IgG and IgM were detected separately by double staining with IgG FITC and IgM R-PE. If the s/c value ≥ 0.9 but < 1.0 it is considered to be weak reactive (+); the s/c value of 1.0 or greater is considered positive +. The weak reactivity (+) by EIA means that the sample is positive in some tests and negative in others.

TABLE 2

Comparison between r-FIFA and FDA licensed confirmatory tests based on
sensitivity for detection of antibodies to HIV-1 proteins encoded in the
three open reading frames of HIV-1 genome in the anti-HIV-1 low titer panel PRB104

| PRB104 I.D. Number | BioRad WB* | | | | Ortho/Cambridge WB | | | | Organon Teknika WB | | | | HIV-1 RIPA RL15 | | | | HIV-1 r-FIFA | | | |
|---|---|---|---|---|---|---|---|---|---|---|---|---|---|---|---|---|---|---|---|---|
| | gag | pol | env | Res. | gag | pol | env | Res. | gag | pol | env | Res. | gag | pol | env | Res. | gag | pol | env[†] | Res. |
| 01 | + | − | + | + | + | + | + | + | + | − | + | + | + | − | + | + | + | + | + | + |
| 02 | + | − | + | + | + | − | + | + | + | − | + | + | + | − | + | + | + | − | + | + |
| 03 | + | − | + | + | + | − | + | + | + | + | + | + | + | + | + | + | + | − | + | + |
| 04 | + | − | + | + | + | − | + | + | + | − | + | + | + | − | + | + | + | + | + | + |
| 05 | + | − | + | + | + | + | + | + | + | + | + | + | + | + | + | + | + | + | + | + |
| 06 | + | + | + | + | + | − | + | + | + | + | + | + | + | + | + | + | + | + | + | + |
| 07 | + | − | − | IND | + | − | − | IND | + | − | − | IND | − | − | + | IND | + | + | + | + |
| 08 | − | − | − | − | + | − | − | IND | + | − | − | IND | − | − | + | IND | + | + | + | + |
| 09 | + | − | + | + | + | − | + | + | + | − | + | + | − | − | + | IND | + | + | + | + |
| 10[‡] | − | − | − | − | − | − | − | − | − | − | − | − | − | − | − | − | − | − | − | − |
| 11 | + | − | + | + | + | − | + | + | + | − | + | + | − | − | + | + | + | − | + | + |
| 12 | + | − | + | + | + | − | + | + | + | − | + | + | + | + | + | + | + | − | + | + |
| 13 | + | − | + | + | + | − | − | IND | + | − | f160 | + | − | − | + | IND | + | + | + | + |
| 14 | f24 | − | − | IND | − | − | − | − | f24 | − | − | IND | − | − | + | IND | + | − | − | IND |
| 15 | − | − | − | − | − | − | − | − | − | − | − | − | − | − | − | − | − | − | − | − |
| TOTAL POSITIVES | 12 | 1 | 10 | 10 | 12 | 2 | 9 | 9 | 13 | 3 | 10 | 10 | 8 | 4 | 13 | 8 | 13 | 8 | 12 | 12 |
| gag + env + = | 71% | | | | 64% | | | | 71% | | | | 57% | | | | 86% | | | |
| gag + pol + env + = | 7% | | | | 14% | | | | 21% | | | | 29% | | | | 57% | | | |

*Western Blots were interpreted using CDC/ASTPHLD criteria. All Western Blots were performed at Boston Biomedica.
[†]The chimeric gag-gp41(C, B) was used for detection of antibodies to env. Later, the results were confirmed using insoluble gp160 polyprotein as antigen in r-FIFA.
[‡]PRB104 10 is the negative control.
f = faint, + = positive, − = negative, IND = indeterminate, RES = result

TABLE 3

Detection of Antibodies to HIV-1 in Samples of Anti-HIV-1 Low Titer Performance Pabels (PRB104) using Different Antigens

| | ANTIGENS | | | | |
|---|---|---|---|---|---|
| PRB104 I.D. NUMBER | gag-p45 s/c | gag-gp41-C s/c | pol97 s/c | gp160 s/c | mixture of gag-p45, pol97 and gp160 s/c |
| 01 | 1.64 | 1.18 | 1.10 | 1.17 | ND |
| 02 | 1.35 | 1.20 | 0.80 | 1.24 | ND |
| 03 | 1.11 | 1.29 | 0.87 | 1.00 | 2.30 |
| 04 | 1.31 | 1.31 | 1.10 | 1.37 | ND |
| 05 | 1.49 | 1.08 | 1.47 | 1.03 | ND |
| 06 | 2.20 | 1.22 | 1.70 | 1.23 | ND |
| 07 | 1.27 | 1.00 | 1.80 | 1.00 | 1.36 |
| 08 | 1.36 | 1.06 | 1.24 | 1.22 | ND |
| 09 | 1.34 | 1.00 | 1.32 | 1.00 | ND |
| 10 | 0.89 | 0.63 | 0.61 | 0.72 | 0.71 |
| 11 | 1.45 | 1.04 | 0.80 | 1.00 | 1.46 |
| 12 | 1.38 | 1.06 | 0.79 | 1.16 | ND |
| 13 | 1.59 | 0.93 | 1.47 | 1.22 | ND |
| 14 | 1.09 | 0.78 | 0.58 | 0.78 | 1.16 |
| 15 | 0.81 | 0.77 | 0.86 | 0.54 | ND |

TABLE 4

Comparison of Sensitivity Between Licensed Tests and r-FIFA in Detection of Antibodies to HBc

| MEMBER I.D. NUMBER | MA-TRIX | ANTI-HBc IgM ABBOTT EIA PROC A (S/CO) BBI | ANTI-HBc IgM ABBOTT EIA PROC B (S/CO) BBI | ANTI-HBc IgM ABBOTT EIA PROC B (S/CO) RL1 | ANTI-HBc IgM ABBOTT RIA PROC A (S/CO) BBI | ANTI-HBc IgM ABBOTT RIA PROC B (S/CO) BBI | ANTI-HBc IgM ABBOTT RIA PROC B (S/CO) RL1 | ANTI-HBc IgM SORIN EIA BBI | HBsAg ABBOTT RIA PROC A (S/CO) BBI | ANTI-HBs ABBOTT EIA PROC B (S/CO) BBI | ANTI-HBc r-FIFA IgG (s/c) | ANTI-HBc r-FIFA IgM (s/c) |
|---|---|---|---|---|---|---|---|---|---|---|---|---|
| PHE201-01 | P | 4.5 | 4.8 | 4.7 | 5.8 | 5.3 | 9.2 | 8.2 | 114 | 0.2 | 5.6 | 2.7 |
| PHE201-02 | P | 4.0 | 3.9 | 4.6 | 4.8 | 5.1 | 6.0 | 9.9 | 99 | 0.2 | 8.7 | 2.71 |
| PHE201-03 | P | 13.0 | 5.5 | 4.6 | 11.5 | 12.7 | 13.1 | 12.0 | 100 | 0.2 | 7.33 | 6.09 |
| PHE201-04 | P | 0.4 | 0.5 | 0.6 | 0.5 | 0.5 | 0.6 | 2.2 | 131 | 0.4 | 0.58 | 0.52 |
| PHE201-05 | P | 6.5 | 5.1 | 4.6 | 5.0 | 6.0 | 8.2 | 10.1 | 5 | 0.2 | 6.93 | 4.66 |
| PHE201-06 | P | 3.0 | 3.0 | 4.1 | 3.3 | 2.7 | 4.2 | 7.9 | 106 | 0.2 | 5.55 | 2.11 |
| PHE201-07 | P | 2.7 | 2.4 | 3.7 | 3.7 | 4.0 | 4.3 | 8.6 | 26 | 0.1 | 6.83 | 2.46 |
| PHE201-08 | P | 3.7 | 3.3 | 4.6 | 3.5 | 4.3 | 5.9 | 10.5 | 117 | 0.2 | 7.60 | 4.19 |
| PHE201-09 | S | 3.7 | 3.5 | 4.3 | 3.7 | 3.5 | 5.0 | 9.6 | 129 | 0.1 | 7.08 | 2.84 |
| PHE201-10 | P | 1.5 | 1.8 | 3.5 | 1.6 | 1.9 | 4.5 | 5.3 | 98 | 0.2 | 3.87 | 2.72 |
| PHE201-11 | P | 0.4 | 0.5 | 0.8 | 0.4 | 0.4 | 0.5 | 1.8 | 94 | 0.6 | 3.72 | 0.81 |
| PHE201-12 | P | 7.3 | 5.5 | 4.7 | 6.7 | 7.8 | 9.1 | 10.1 | 15 | 0.2 | 3.62 | 4.71 |
| PHE201-13 | P | 5.5 | 4.4 | 4.7 | 6.8 | 5.2 | 7.3 | 10.4 | 88 | 0.2 | 8.60 | 4.71 |
| PHE201-14 | P | 5.8 | 5.1 | 4.7 | 5.6 | 6.3 | 8.0 | 10.6 | 96 | 0.2 | 4.44 | 3.42 |
| PHE201-15 | S | 8.5 | 8.1 | 4.7 | 9.0 | 10.0 | 10.8 | 11.2 | 113 | 0.1 | 9.25 | 5.94 |
| PHE201-16 | P | 9.1 | 5.5 | 4.7 | 8.3 | 8.4 | 10.8 | 11.0 | 103 | 0.2 | 9.77 | 5.16 |
| PHE201-17 | P | 5.1 | 5.0 | 4.7 | 7.0 | 7.1 | 8.9 | 10.9 | 103 | 0.2 | 8.55 | 3.64 |
| PHE201-18 | S | 1.8 | 1.9 | 2.6 | 1.7 | 2.0 | 2.6 | 6.8 | 80 | 0.1 | 6.65 | 2.6 |
| PHE201-19 | S | 3.9 | 3.0 | 4.1 | 3.0 | 3.0 | 4.8 | 8.5 | 108 | 0.2 | 5.04 | 3.54 |
| PHE201-20 | S | 2.2 | 2.4 | 2.6 | 2.2 | 2.7 | 2.1 | 6.3 | 117 | 0.2 | 7.88 | 2.59 |
| PHE201-21 | P | 3.1 | 2.8 | 3.3 | 2.7 | 2.5 | 3.7 | 8.2 | 128 | 0.1 | 5.41 | 2.11 |
| PHE201-22 | P | 2.5 | 3.1 | 3.1 | 2.6 | 2.4 | 3.7 | 8.9 | 101 | 0.2 | 1.54 | 1.17 |
| PHE201-23 | P | 2.1 | 2.3 | 2.8 | 2.8 | 2.7 | 2.6 | 6.1 | 152 | 0.2 | 6.55 | 1.89 |
| PHE201-24 | P | 3.8 | 2.8 | 3.8 | 2.5 | 3.4 | 4.0 | 8.9 | 113 | 0.3 | 2.69 | 1.87 |
| PHE201-25 | P | 2.7 | 3.1 | 4.2 | 2.9 | 3.3 | 4.3 | 10.3 | 114 | 0.2 | 9.13 | 4.89 |

All panel members have been found positive by a test for HBsAg and negative by a test for anti-HIV-1.
EIA and RIA results were generated using commercially available FDA approved anti-HBc IgM screening tests, performed at BBI and at a nationally recognized non-commercial referee laboratory (RL1) by individuals who routinely use these procedures. All numeric results are means of duplicates, expressed as specimen absorbance to cutoff ratios (s/co). Ratios ≥ 1.0 are considered reactive.
Specimens are undiluted aliquots form serum (S) or plasma (P) units collected from asymptomatic blood donors in 1989 and 1990.

The embodiments of the invention in which an exclusive property or privilege is claimed are defined as follows:

1. A method for detection of a disease state which comprises utilizing an insoluble form of at least one recombinant protein in a flow cytometric immunofluorescence assay, said method comprising:

(i) obtaining a sample of biological fluid within which the disease state is to be detected;

(ii) adding a predetermined amount of said insoluble form of at least one recombinant protein to said sample to form a mixture, wherein said insoluble form being produced in particle form by expression in baculovirus or in an expression system producing a particle form, and wherein said insoluble form is the carrier and the antigen;

(iii) incubating said mixture for a period of time sufficient to permit association between said insoluble form of at least one recombinant protein and antibodies within said sample to form an incubated mixture;

(iv) washing said incubated mixture;

(v) adding a labelled antibody to the mixture of step (iv) and incubating for a period of time sufficient for said labeled antibody to bind with antibodies within said incubated mixture to form a labeled mixture;

(vi) washing said labeled mixture;

(vii) detecting IgM complexes formed in said washed labeled mixture using flow cytometric immunofluorescence; and (viii) correlating detection of IgM complexes with a disease state, wherein an increase level of IgM over the control level is indicative of the disease state.

2. The method of claim 1 wherein the recombinant protein is expressed in a baculovirus.

3. The method of claim 1 wherein the disease state is selected from the group consisting of HIV infection, hepatitis and HTLV infection.

4. The method of claim 3 wherein the disease is selected from the group consisting of HIV-1 infection, HIV-2 infection, hepatitis B infection, hepatitis C infection, HTLV-1 infection and HTLV-2 infection.

5. The method of claim 4 wherein the disease state is HIV-1 infection.

6. The method of claim 4 wherein the disease state is hepatitis B infection.

7. The method of claim 3, wherein the disease state is HIV infection and the said at least one recombinant protein comprises po197, gp160, or a protein comprising SEQ ID NO:2, optionally fused to an amino acid sequence of a selected fusion protein having a sequence selected from the group consisting of SEQ ID NO: 4, SEQ ID NO: 6, and SEQ ID NO: 8; or mixtures thereof, and variants thereof.

8. The method of claim 7 wherein a mixture of gag-p45, po197 and gp160 is utilized as carrier and antigen.

9. The method of claim 7, wherein said recombinant protein further comprises an amino acid sequence of SEQ ID NO:4 as the selected fusion partner.

10. The method of claim 7, wherein said recombinant protein further comprises an amino acid sequence of SEQ ID NO:6 as the selected fusion partner.

11. The method of claim 7, wherein said recombinant protein further comprises an amino acid sequence of SEQ ID NO:8 as the selected fusion partner.

12. The method of claim 7, wherein the selected fusion partner has at least one immunoreactive domain.

* * * * *